United States Patent
Lunde et al.

(10) Patent No.: US 10,450,539 B2
(45) Date of Patent: Oct. 22, 2019

(54) USE OF M4 METALLOPROTEASE IN WORT PRODUCTION

(71) Applicant: Novozymes A/S, Bagsvaerd (DK)

(72) Inventors: Christina Lunde, Copenhagen (DK); Morten Gjermansen, Greve (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 15/572,872

(22) PCT Filed: Jun. 3, 2016

(86) PCT No.: PCT/EP2016/062635
§ 371 (c)(1),
(2) Date: Nov. 9, 2017

(87) PCT Pub. No.: WO2016/193420
PCT Pub. Date: Dec. 8, 2016

(65) Prior Publication Data
US 2018/0119073 A1    May 3, 2018

(30) Foreign Application Priority Data

Jun. 4, 2015 (EP) .................................. 15170654

(51) Int. Cl.
*C12C 7/04*  (2006.01)
*C12C 5/00*  (2006.01)
*C12C 7/00*  (2006.01)
*C12N 9/52*  (2006.01)

(52) U.S. Cl.
CPC .............. *C12C 5/004* (2013.01); *C12C 5/006* (2013.01); *C12C 7/00* (2013.01); *C12C 7/04* (2013.01); *C12N 9/52* (2013.01); *C12Y 302/01* (2013.01); *C12Y 302/01001* (2013.01); *C12Y 302/01008* (2013.01); *C12Y 302/01041* (2013.01); *C12Y 304/24* (2013.01)

(58) Field of Classification Search
CPC .. C12C 5/004; C12C 7/00; C12C 7/04; C12C 5/006
USPC ................................ 426/7, 11, 16, 592, 29
See application file for complete search history.

(56) References Cited

U.S. PATENT DOCUMENTS

2010/0303955 A1    12/2010  Elvig
2014/0024103 A1*    1/2014  Benie .................... C11D 3/386
                                                            435/263

FOREIGN PATENT DOCUMENTS

| WO | 97/29179 A1 | 8/1997 |
| WO | 2009/074650 A2 | 6/2009 |
| WO | 2010/094773 A2 | 8/2010 |
| WO | 2013/167573 A1 | 11/2013 |
| WO | 2014/191298 A1 | 12/2014 |

OTHER PUBLICATIONS

Fischbach et al., UniProt accession No. B5HMH0 (2008).
Lee, UniProt accession No. A0A0B1ZBN3 (2015).
Lucas et al., UniProt accession No. D2PND2 (2010).
O'Brien et al., UniProt accession No. K1V085 (2012).
Omura et al., UniProt accession No. Q82BN5 (2003).
Omura et al., UniProt accession No. Q82BS4 (2003).
Sweeney et al., UniProt accession No. A0A0B5DR96 (2015).

* cited by examiner

*Primary Examiner* — Vera Stulii
(74) *Attorney, Agent, or Firm* — Kelly Reynolds

(57) ABSTRACT

A method of preparing a wort with an increased level of free amino nitrogen (FAN) comprising: a) preparing a mash from a grist comprising malt and/or adjunct; and b) adding a M4 mettalloprotease obtainable from Actinobacteria; and wherein the amount of free amino nitrogen (FAN) in the wort is increased as compared to a wort produced in the absence of the M4 metalloprotease.

16 Claims, No Drawings
Specification includes a Sequence Listing.

USE OF M4 METALLOPROTEASE IN WORT PRODUCTION

CROSS-REFERENCE TO RELATED APPLICATIONS

This application is a 35 U.S.C. 371 national application of international application no. PCT/EP2016/062635 filed Jun. 3, 2016, which claims priority or the benefit under 35 U.S.C. 119 of European application no. 5170654.6 filed Jun. 4, 2015. The contents of each application are fully incorporated herein by reference.

REFERENCE TO SEQUENCE LISTING

This application contains a Sequence Listing in computer readable form. The computer readable form is incorporated herein by reference.

FIELD OF THE INVENTION

This invention relates to wort making for brewing and non-alcoholic beverages. More particularly, it relates to a method of increasing the level of free amino nitrogen in a wort.

BACKGROUND OF THE INVENTION

Modern breweries need to have a high level of raw material flexibility with respect to adjunct inclusion and malt quality.

When adjuncts like corn grits, barley or rice are used in the brewing process instead of malt, or when under-modified low quality malt is used, this will result in a level of free amino nitrogen that is insufficient to have proper yeast fermentation.

Wort nitrogen is normally determined as FAN (free amino nitrogen). FAN includes all free primary amines and thus also includes amines of nucleotides and other compounds which are not amino acids.

The inventors have found a surprisingly good method of increasing the level of FAN in a wort.

SUMMARY OF THE INVENTION

Surprisingly, it has been found that it is possible to significantly increase the level of FAN in a wort, so we claim:

A method of preparing a wort with an increased level of free amino nitrogen (FAN) comprising:
 a) preparing a mash from a grist comprising malt and/or adjunct; and
 b) adding an M4 metalloprotease obtainable from Actinobacteria; and
wherein the amount of free amino nitrogen (FAN) in the wort is increased as compared to a wort produced in the absence of the M4 metalloprotease.

In one embodiment, the M4 metalloprotease has at least 80% sequence identity to the mature polypeptide selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11.

In one embodiment, the M4 metalloprotease is a variant of the polypeptide of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11, comprising a substitution, deletion, and/or insertion at one or more positions.

In one embodiment, the M4 metalloprotease consists of the polypeptide of SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11.

In one embodiment, the M4 metalloprotease according to the invention is added to the mash or to the wort.

In one embodiment, additionally an alpha amylase is added to the mash.

In one embodiment, additionally a beta glucanase is added to the mash.

In one embodiment, additionally a pullulanase is added to the mash.

In one embodiment, additionally a xylanase is added to the mash.

In one embodiment, additionally a lipase is added to the mash.

In one embodiment, the M4 metalloprotease is added in an amount of 1-100 mg enzyme protein per kg grist.

In one embodiment, the grist comprises at least 10% (w/w) adjunct.

In one embodiment, the adjunct is selected from the group consisting of barley, rice, corn, wheat, sorghum and cassava.

In one embodiment, the wort is fermented to obtain a beer.

In one embodiment, the mashing is done in the absence of a protein rest.

In one embodiment, the amount of free amino nitrogen (FAN) is increased by at least 20% when the M4 metalloprotease according to the invention is added in an amount of 10 mg Enzyme Protein per kg grist as compared to a wort produced in the absence of the M4 metalloprotease according to the invention.

The invention also describes use of an M4 metalloprotease obtainable from Actonobacteria in wort production.

DEFINITIONS

Polypeptides Having Protease Activity

Polypeptides having protease activity, or proteases, are sometimes also designated peptidases, proteinases, peptide hydrolases, or proteolytic enzymes.

The term "protease" is defined herein as an enzyme that hydrolyses peptide bonds. This definition of protease also applies to the protease-part of the terms "parent protease" and "protease variant," as used herein. The term "protease" includes any enzyme belonging to the EC 3.4 enzyme group (including each of the thirteen subclasses thereof). The EC number refers to Enzyme Nomenclature 1992 from NC-IUBMB, Academic Press, San Diego, Calif., including supplements 1-5 published in Eur. J. Bio-chem. 1994, 223, 1-5; Eur. J. Biochem. 1995, 232, 1-6; Eur. J. Biochem. 1996, 237, 1-5; Eur. J. Biochem. 1997, 250, 1-6; and Eur. J. Biochem. 1999, 264, 610-650. The nomenclature is regularly supplemented and updated; see, e.g., the World Wide Web (WWW) at http://www.chem.qmw.ac.uk/iubmb/enzyme/index.html.

Protease activity can be measured using any assay, in which a substrate is employed, that includes peptide bonds relevant for the specificity of the protease in question. Assay-pH and assay-temperature are likewise to be adapted to the protease in question. Examples of assay-pH-values are pH 2, 3, 4, 5, 6, 7, 8, 9, 10, 11, or 12. Examples of assay-temperatures are 15, 20, 25, 30, 35, 37, 40, 45, 50, 55, 60, 65, 70, 80, 90, or 95° C. Examples of protease substrates are casein, such as Azurine-Crosslinked Casein (AZCL-casein).

Protease activity: The term "protease activity" means a proteolytic activity that catalyzes the hydrolysis of amide bond or a protein by hydrolysis of the peptide bond that link amino acids together in a polypeptide chain. Several assays for determining protease activity are available in the art. For purposes of the present invention, protease activity may be determined using Protazyme AK tablet (cross-linked and dyed casein; from Megazyme).

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Catalytic domain: The term "catalytic domain" means the region of an enzyme containing the catalytic machinery of the enzyme.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide having one or more (e.g., several) amino acids absent from the amino and/or carboxyl terminus of a mature polypeptide or domain; wherein the fragment has protease activity.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Mature polypeptide: The term "mature polypeptide" means a polypeptide in its final form following translation and any post-translational modifications, such as N-terminal processing, C-terminal truncation, glycosylation, phosphorylation, etc.

Mature polypeptide coding sequence: The term "mature polypeptide coding sequence" means a polynucleotide that encodes a mature polypeptide having protease activity.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide in such a way that the control sequence directs expression of the coding sequence.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment).

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment).

Subsequence: The term "subsequence" means a polynucleotide having one or more (e.g., several) nucleotides absent from the 5' and/or 3' end of a mature polypeptide coding sequence; wherein the subsequence encodes a fragment having protease activity.

Variant: The term "variant" means a polypeptide having protease activity comprising an alteration, i.e., a substitution, insertion, and/or deletion, at one or more (e.g., several) positions, e.g., a substitution, insertion, and/or deletion at 10 positions; or a substitution, insertion, and/or deletion at 9 positions; or a substitution, insertion, and/or deletion at 8 positions; or a substitution, insertion, and/or deletion at 7 positions; or a substitution, insertion, and/or deletion at 6 positions; or a substitution, insertion, and/or deletion at 5 positions; or a substitution, insertion, and/or deletion at 4 positions; or a substitution, insertion, and/or deletion at 3 positions; or a substitution, insertion, and/or deletion at 2 positions; or a substitution, insertion, and/or deletion at 1 position.

A substitution means replacement of the amino acid occupying a position with a different amino acid; a deletion means removal of the amino acid occupying a position; and an insertion means adding one or more (e.g. several) amino acids, e.g., 1-5 amino acids adjacent to and immediately following the amino acid occupying a position.

Beverage: The term beverage as used herein has the conventional meaning in the art and includes, but is not limited to beer, and any wort based beverage.

Beer: The term "beer" as used herein is intended to cover at least beer prepared from mashes prepared from unmalted cereals as well as all mashes prepared from malted cereals, and all mashes prepared from a mixture of malted and unmalted cereals. The term "beer" also covers beers prepared with adjuncts, and beers with all possible alcohol contents.

Grist: The term "grist" is understood as the starch or sugar containing material that is the basis for beer production, e.g., the barley malt and/or the adjunct. Generally, the grist does not contain any added water.

Malt: The term "malt" is understood as any malted cereal grain, in particular barley.

Adjunct: The term "adjunct" is understood as the part of the grist which is not barley malt. The adjunct may be any starch rich plant material, e.g., unmalted grain, such as, but not limited to, barley, corn, rice, sorghum, wheat and cassava, and also includes readily fermentable sugar and/or syrup. The starch of some of the adjuncts has a relatively low gelatinization temperature which enable them to be mashed in together with the malt, whereas other adjuncts such as rice, corn and sorghum has a higher gelatinization temperature, such adjuncts are typically separately cooked and liquefied with an alpha-amylase before they are added to the mash.

Mash: The term "mash" is understood as a starch containing slurry comprising crushed barley malt, and/or crushed unmalted grain, and/or other starch containing material, or a combination hereof, steeped in water to make wort.

Protein rest: The term "protein rest" is understood as a part of the mashing process.

Typically, it is the first step in mashing. It is performed at a temperature of around 45° C. to 55° C. for normally 15 to 30 minutes.

Wort: The term "wort" is understood as the unfermented liquor run-off following extracting the grist during mashing.

DETAILED DESCRIPTION OF THE INVENTION

The advantage of the present invention is that it allows the breweries to have a higher level of raw material flexibility with respect to adjunct inclusion and malt quality.

When adjuncts like corn grits, barley, or rice are included in the brewing process instead of malt, the level of FAN (free amino nitrogen) will be insufficient to have proper yeast fermentation. The same issue occurs when an under-modified low quality malt is used.

During traditional mashing, the endogenous malt proteases are capable of increasing the overall FAN level. This increase occurs mainly during the protein rest (e.g., 20 min, 50° C.).

Adding the M4 metalloprotease according to the invention to the mash may allow the breweries to eliminate the protein rest without losing FAN. Eliminating the protein rest will save time and energy in the brewing process and also minimize the lipoxygenase (LOX) catalyzed lipid oxidation leading to off-flavors in the final product.

Wort Production

The present invention relates to a method of producing a wort with an increased level of FAN, wherein an M4 metalloprotease obtainable from Actinobacteria, in particular an M4 metalloprotease that has at least 80% sequence identity to the polypeptide selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11, has been added to the mash or the wort.

In a preferred embodiment, the present invention relates to a method of producing a wort with an increased level of FAN, wherein an M4 metalloprotease that has at least 80% sequence identity to the mature polypeptide selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11, has been added to the mash or the wort.

The mash is obtainable by grinding a grist comprising malt and/or adjunct. Water may preferably be added to the grist, and is normally preheated in order for the mash to attain the desired mash temperature at the moment of mash forming. If the temperature of the formed mash is below the desired mashing temperature, additional heat is preferably supplied in order to attain the desired process temperature.

The temperature profile of the mashing process may be a profile from a conventional mashing process wherein the temperatures are set to achieve optimal degradation of the grist dry matter by the malt enzymes and/or the added enzymes.

The malt is preferably derived from one or more of the grains selected from the list consisting of, e.g., corn, barley, wheat, rye, sorghum, millet and rice, or any mixtures thereof.

Preferably, the malt is barley malt. The grist preferably comprises from 0.5% to 99% (w/w) malt, e.g., from 1% to 95% (w/w) malt, e.g., from 5% to 90% (w/w) malt, e.g., from 10% to 85% (w/w) malt, e.g., from 15% to 80% (w/w) malt, e.g., from 20% to 75% (w/w) malt, from 25% to 70% (w/w) malt, e.g., from 30% to 65% (w/w) malt.

In addition to malted grain, the grist may comprise one or more adjuncts such as unmalted corn, or other unmalted grain, such as barley, wheat, rye, oat, corn, rice, milo, millet and/or sorghum, or raw and/or refined starch and/or sugar containing material derived from plants like wheat, rye, oat, corn, rice, milo, millet, sorghum, pea, potato, sweet potato, cassava, tapioca, sago, banana, sugar beet and/or sugar cane. According to the present invention, adjuncts may be obtained from tubers, roots, stems, leaves, legumes, cereals and/or whole grain.

Preferred is adjunct obtained from barley, corn, rice, wheat, sorghum and/or cassava; e.g., rice starch, corn starch, and/or corn grits.

The grist comprises typically from 1% to 80% (w/w) adjunct, e.g., from 5% to 75% (w/w) adjunct, e.g., from 10% to 70% (w/w) adjunct; in a particular embodiment the grist comprises at least 10% (w/w) adjunct. In a preferred embodiment, the grist comprises from 30% to 70% (w/w) adjunct.

In one aspect, the M4 metalloprotease according to the invention is introduced at the beginning of mashing. In another aspect, the M4 metalloprotease according to the invention is introduced during mashing. In another aspect, the M4 metalloprotease according to the invention is added to the wort.

The amount of added M4 metalloprotease according to the invention generally depends on various factors. For purposes of this invention, the amount of M4 metalloprotease used will generally be of from 0.1 mg to 100 mg EP (Enzyme Protein) per kg grist, preferably from 1 mg to 100 mg EP (Enzyme Protein) per kg grist; preferably from 1 mg to 50 mg EP (Enzyme Protein) per kg grist.

In a preferred embodiment, the amount of free amino nitrogen in the wort is increased by at least 20% (when the protease according to the invention is added in an amount of 10 mg Enzyme Protein per kg grist) as compared to a wort produced in the absence of the protease according to the invention, e.g., the amount of free amino nitrogen in the wort is increased by at least 30% (when the protease according to the invention is added in an amount of 10 mg Enzyme Protein per kg grist) as compared to a wort produced in the absence of the protease according to the invention, e.g., the amount of free amino nitrogen in the wort is increased by at least 40% (when the protease according to the invention is added in an amount of 10 mg Enzyme Protein per kg grist) as compared to a wort produced in the absence of the protease according to the invention, e.g., the amount of free amino nitrogen in the wort is increased by at least 50% (when the protease according to the invention is added in an amount of 10 mg Enzyme Protein per kg grist) as compared to a wort produced in the absence of the protease according to the invention.

In another preferred embodiment, a further enzyme(s) is added to the mash, said enzyme(s) including but not limited to alpha amylase, isoamylase, maltogenic amylase, protease, cellulase, beta glucanase, pullulanase, laccase, xylanase, lipase, phospholipase, phytase, and esterase.

In one aspect of the method, the further enzyme added includes a pullulanase.

In one aspect of the method, the further enzyme added includes an amylase, preferably an alpha amylase.

In one aspect of the method, the further enzyme added includes a beta glucanase.

In one aspect of the method, the further enzyme added includes a xylanase.

In one aspect of the method, the further enzyme added includes a lipase.

Following the separation of the wort from the spent grains of the grist, the wort may be used as it is or it may be dewatered to provide a concentrated and/or dried wort. The concentrated and/or dried wort may be used as brewing extract, as malt extract flavoring, for non-alcoholic malt beverages, malt vinegar, breakfast cereals, for confectionary, etc.

In a preferred embodiment, the wort is fermented to produce an alcoholic beverage, preferably a beer, e.g., ale, strong ale, bitter, stout, porter, lager, export beer, malt liquor, barley wine, happoshu, high-alcohol beer, low-alcohol beer, low-calorie beer or light beer.

Fermentation of the wort may include pitching the wort with a yeast slurry comprising fresh yeast, i.e., yeast not previously used or the yeast may be recycled yeast. The yeast applied may be any yeast suitable for beer brewing, especially yeasts selected from *Saccharomyces* spp. such as *S. cerevisiae* and *S. uvarum*, including natural or artificially produced variants of these organisms.

The methods for fermentation of wort for production of beer are well known to the person skilled in the art.

Actinobacteria

Actinobacteria are a specific class of bacteria. Morphologically, they often resemble fungi because of their elongated cells that branch into filaments or hyphae.

Actinobacteria comprise the orders of Propionibacteriales, Streptomycetales, and Micromonosporales, which are further subdivided into families and genera.

Actinobacteria comprise the genera *Streptomyces, Nocardia, Kitasatospora, Actinoplanes, Dactylosporangium, Micromonospora, Kribbella, Nocardioides, Propionibacterium, Nocardiopsis, Streptomonospora*, and *Thermobifida*.

The M4 metalloprotease according to the present invention is obtainable from Actinobactera; in particular the M4 metalloprotease is selected from the group consisting of *Streptomyces, Nocardia, Kitasatospora, Actinoplanes, Dactylosporangium, Micromonospora, Kribbella, Nocardioides, Propionibacterium, Nocardiopsis, Streptomonospora*, and *Thermobifida*.

Proteases According to the Invention

The M4 metalloprotease according to the present invention is obtainable from Actinobacteria; in particular the M4 metalloprotease is obtainable from *Streptomyces, Nocardia, Kitasatospora, Actinoplanes, Dactylosporangium, Micromonospora, Kribbella, Nocardioides, Propionibacterium, Nocardiopsis, Streptomonospora*, or *Thermobifida*.

A protease may be classified as an M4 meatalloprotease as known in the art, e.g., by using the MEROPS database: http://merops.sanger.ac.uk/cgi-bin/blast/submitblast/merops/advanced The MEROPS database is described in "Twenty years of the MEROPS database of proteolytic enzymes, their substrates and inhibitors"; Rawlings N D, Barrett A J, Finn R.; Nucleic Acids Res; 2016 Jan. 4; 44(D1):D343-50.

In one embodiment, the present invention relates to an isolated polypeptide having a sequence identity to the polypeptide selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11 of at least 80%, e.g., of at least 81%, e.g., of at least 82%, e.g., of at least 83%, e.g., of at least 84%, e.g., of at least 85%, e.g., of at least 86%, e.g., of at least 87%, e.g., of at least 88%, e.g., of at least 89%, e.g., of at least 90%, e.g., of at least 91%, e.g., of at least 92%, e.g., of at least 93%, e.g., of at least 94%, e.g., of at least 95%, e.g., of at least 96%, e.g., of at least 97%, e.g., of at least 98%, e.g., of at least 99%, or 100% identical, and wherein the polypeptide has protease activity.

In one embodiment, the present invention relates to an isolated polypeptide having a sequence identity to the mature polypeptide selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11 of at least 80%, e.g., of at least 81%, e.g., of at least 82%, e.g., of at least 83%, e.g., of at least 84%, e.g., of at least 85%, e.g., of at least 86%, e.g., of at least 87%, e.g., of at least 88%, e.g., of at least 89%, e.g., of at least 90%, e.g., of at least 91%, e.g., of at least 92%, e.g., of at least 93%, e.g., of at least 94%, e.g., of at least 95%, e.g., of at least 96%, e.g., of at least 97%, e.g., of at least 98%, e.g., of at least 99%, or 100% identical, and wherein the polypeptide has protease activity.

A polypeptide of the present invention preferably comprises or consists of the amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11; or is an allelic variant thereof; or is a fragment thereof having protease activity.

In another embodiment, the present invention relates to an isolated polypeptide having protease activity encoded by a polynucleotide that hybridizes under low stringency conditions, medium stringency conditions, medium-high stringency conditions, or high stringency conditions with the polypeptide coding sequence of SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11, or the full-length complement thereof (Sambrook et al., 1989, *Molecular Cloning, A Laboratory Manual,* 2d edition, Cold Spring Harbor, N.Y.).

In another embodiment, the present invention relates to variants of the polypeptide of SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11, comprising a substitution, deletion, and/or insertion at one or more (e.g., several) positions.

In one embodiment, the number of amino acid substitutions, deletions and/or insertions introduced into the polypeptide of SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11, is not more than 20, e.g., 1, 2, 3, 4, 5, 6, 7, 8, 9, 10, 11, 12, 13, 14, 15, 16, 17, 18, 19, or 20.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope, or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins,* Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for protease activity to identify amino acid residues that are critical to the activity of the molecule. See also, Hilton et al., 1996, *J. Biol. Chem.* 271: 4699-4708.

The active site of the enzyme or other biological interaction can also be determined by physical analysis of structure, as determined by such techniques as nuclear magnetic resonance, crystallography, electron diffraction, or photo-affinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779). A fusion polypeptide can further comprise a cleavage site between the two polypeptides.

Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Enzyme Compositions

The present invention also relates to compositions comprising the M4 metalloprotease of the present invention for use in wort production.

The compositions according to the invention may comprise the M4 metalloprotease of the present invention as the major enzymatic component, e.g., a mono-component composition.

Alternatively, the compositions may comprise multiple enzymatic activities, such as one or more (e.g., several) enzymes selected from the group consisting of hydrolase, isomerase, ligase, lyase, oxidoreductase, or transferase, e.g., an alpha-galactosidase, alpha-glucosidase, amylase, alpha amylase, beta-galactosidase, beta-glucosidase, beta-xylosidase, carbohydrase, carboxypeptidase, catalase, cellobiohydrolase, cellulase, beta glucanase, chitinase, cutinase, cyclodextrin glycosyltransferase, deoxyribonuclease, endoglucanase, esterase, glucoamylase, invertase, laccase, lipase, mannosidase, mutanase, oxidase, peroxidase, phytase, polyphenoloxidase, pullulanase, ribonuclease, transglutaminase, or xylanase.

Preferably, the composition for use in wort production may comprise an M4 metalloprotease obtainable from Actinobacteria; in particular an M4 metalloprotease having at least 80% sequence identity to the polypeptide of SEQ ID NO: 1; SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11; or the composition for use in wort production may comprise the M4 metalloprotease according to the invention and one or more enzymes selected from the group consisting of alpha amylase, beta glucanase, pullulanase, xylanase, and lipase.

The compositions may be prepared in accordance with methods known in the art and may be in the form of a liquid or a dry composition. The compositions may be stabilized in accordance with methods known in the art. The dosage of the composition and other conditions under which the composition is used may be determined on the basis of methods known in the art.

The present invention is further described by the following examples that should not be construed as limiting the scope of the invention.

EXAMPLE 1

Cloning and Expression of M4 Metalloproteases from Bacterial Strains from the Class Actinobacteria The metalloproteases were derived from bacterial strains obtained by isolation from environmental sources collected from the locations listed in Table 1.

The strain *Streptomyces thermoalcalitolerans* was obtained from the German collection of Microorganisms and Cell Cultures (DSMZ) as DSM41741 type strain of *Streptomyces thermoalcalitolerans*. This strain was originally isolated from garden soil in Yogyakarta, Indonesia (Kim et al., Classification of thermophilic streptomycetes, including the description of *Streptomyces thermoalcalitolerans* sp. nov., Int. J. Syst. Bacteriol. (1999) 49: 7-17).

TABLE 1

| Organism | Country of isolation |
| --- | --- |
| *Micromonospora* sp.-61168 | United Kingdom |
| *Streptomyces thermoalcalitolerans* | Indonesia |
| *Streptomyces ginsengisoli* | Japan |
| *Kribbella aluminosa* | China |
| *Streptomyces* sp.-61982 | Japan |
| *Streptomyces champavatii* | United Kingdom |
| *Streptomyces kathirae* | United Kingdom |
| *Streptomyces* sp.-62237 | Japan |

Chromosomal DNA from pure cultures of the individual strains were purified and subjected to full genome sequencing using Illumina sequencing technology. The assembled genome sequences and subsequent analysis of the 16S ribosomal subunit gene sequences against the ARB-SILVA database (The SILVA ribosomal RNA gene database project: improved data processing and web-based tools. Quast et al. Nucl. Acids Res. 41 (2013): D590-D596) confirmed the identity of the strains.

The individual genome sequences were analyzed for metalloproteases from the MEROPS family M4 by comparison to the M4 protease NprE from *B. subtilis* 168 (Uniprot P68736) by search using the BLAST program.

This analysis identified genes encoding M4 metalloproteases with the nucleotide sequences given in SEQ ID NO: 12 to 22 and translated proteins sequences in SEQ ID NO:1 to SEQ ID NO:11.

The genes encoding the M4 metalloproteases was amplified from genomic DNA by PCR and fused with regulatory elements and homology regions for recombination into the *B. subtilis* genome.

The linear integration construct was a SOE-PCR fusion product (Horton, R. M., Hunt, H. D., Ho, S. N., Pullen, J. K. and Pease, L. R. (1989) *Engineering hybrid genes without the use of restriction enzymes, gene splicing by overlap extension* Gene 77: 61-68) made by fusion of the gene between two *Bacillus subtilis* chromosomal regions along with strong promoters and a chloramphenicol resistance marker. The SOE PCR method is also described in patent application WO 2003/095658.

The gene was expressed under the control of a triple promoter system (as described in WO 99/43835), consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence.

The gene was expressed with a *Bacillus clausii* secretion signal (encoding the following amino acid sequence: MKKPLGKIVASTALLISVAFSSSIASA) replacing the native secretion signal. The native secretion signals were predicted using the SignalP 3.0 program (Improved prediction of signal peptides: SignalP 3.0, Bendtsen et al. J. Mol. Biol., 340:783-795, 2004) Furthermore, the expression construct results in the addition of a carboxy-terminal poly histidine tail consisting of 6 consecutive histidine residues.

The SOE-PCR product was transformed into *Bacillus subtilis* and integrated in the chromosome by homologous recombination into the pectate lyase locus. Subsequently, a recombinant *Bacillus subtilis* clone containing the integrated expression construct was grown in liquid culture. The culture broth was centrifuged (20000×g, 20 min), and the supernatant was carefully decanted from the precipitate and used for purification of the enzyme or directly in enzyme assays.

The mature expressed protein of the recombinant M4 metalloproteases can be determined by N-terminal amino acid sequencing by Edman degradation and intact molecular weight analysis by mass spectroscopy of the purified protein (Peptide and protein analysis with mass spectrometry, Trauger et al. Spectroscopy, Volume 16 (2002), Issue 1, Pages 15-28.)

EXAMPLE 2

Adding a Protease According to the Invention with Improved Free Amino Nitrogen (FAN) Generation during Small Scale Mashing The proteases according to the invention (prepared according to Example 1) were compared to the protease Neutrase™ (Novozymes A/S) using the following procedure:

1. Add 5 g corn starch to 100 mL Blue Cap bottles with magnetic stirrer.
2. Grind the malt (from Danish Malting Group (Prod nr 2012-0646)) at gap 0.2 mm (Bühler mill) and weigh out 5 g in weighing plastic cups.
3. Add 25 mL 95° C. $H_2O$, 300 µL $CaCl_2$ (0.2 M), and 300 ppm Termamyl™ (Novozymes A/S) to each bottle with 5 g of corn starch
4. Do decoction according to mashing profile (see Table 1 below).
5. Cool down to 50° C. by adding ice or cold water in the water bath, add 5 g of malt, 25 mL 52° C. $H_2O$, 0.3 mL $CaCl_2$, and protease according to set-up (5, 10, and 15 mg enzyme protein/kg grist) to each blue cap bottle.
6. Ready for mashing, set time, and do the mashing manually by setting the temperature on the water bath.
7. Cool down to 30° C. and filtrate with small funnels, 50 mL volumetric cylinders and folded filters (Whatman 597½, ø 185 mm).
8. Measure the level of Free Amino Nitrogen using NOPA assay and a Gallery Plus. (The NOPA assay was Alpha-Amino Nitrogen (NOPA) test kit from Thermo Fisher Scientific (Cat. No. 984342)).

TABLE 1

| Mashing profiles: | |
| --- | --- |
| Temperature [° C.] | Time [min.] |
| Corn Starch - decoction: | |
| 95 | 30 |
| Malt and Corn mashing without a protein rest: | |
| 63 | 50 |
| 72 | 20 |
| 78 | 15 |
| 20 | — |

Results:

TABLE 2

Δ FAN results without a protein rest:
(malt gave a FAN reference level of 105 ppm)

| Protease: | 5 mg EP/ kg grist | 10 mg EP/ kg grist | 15 mg EP/ kg grist |
| --- | --- | --- | --- |
| FAN results with Neutrase | 8 ppm | 12 ppm | 18 ppm |
| FAN results with SEQ ID NO: 3 (mature part) | 35 ppm | 42 ppm | 55 ppm |
| FAN results with SEQ ID NO: 10 (mature part) | 16 ppm | 24 ppm | 29 ppm |
| FAN results with SEQ ID NO: 1 (mature part) | 34 ppm | 50 ppm | 55 ppm |
| FAN results with SEQ ID NO: 5 (mature part) | 29 ppm | 38 ppm | 43 ppm |
| FAN results with SEQ ID NO: 2 (mature part) | 28 ppm | 44 ppm | 49 ppm |
| FAN results with SEQ ID NO: 4 (mature part) | 30 ppm | 38 ppm | 45 ppm |
| FAN results with SEQ ID NO: 6 (mature part) | 21 ppm | 34 ppm | 41 ppm |
| FAN results with SEQ ID NO: 9 (mature part) | 15 ppm | 26 ppm | 32 ppm |
| FAN results with SEQ ID NO: 8 (mature part) | 21 ppm | 32 ppm | 44 ppm |
| FAN results with SEQ ID NO: 11 (mature part) | 10 ppm | 22 ppm | 24 ppm |
| FAN results with SEQ ID NO: 7 (mature part) | 18 ppm | 32 ppm | 46 ppm |

It can be seen from Table 2 that the M4 metalloproteases according to the invention give surprisingly more FAN than Neutrase.

The invention claimed is:

1. A method of preparing a wort with an increased level of free amino nitrogen (FAN) comprising:
   a) preparing a mash from a grist comprising malt and/or adjunct; and
   b) adding an M4 metalloprotease obtainable from Actinobacteria to the mash; and
   wherein the amount of free amino nitrogen (FAN) in the wort is increased as compared to a wort produced in the absence of the M4 metalloprotease.

2. The method according to claim 1, wherein the M4 metalloprotease has at least 80% sequence identity to the mature polypeptide selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11.

3. The method according to claim 1, wherein the M4 metalloprotease is a variant of the polypeptide of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11 comprising a substitution, deletion, and/or insertion at one or more positions.

4. The method according to claim 1, wherein the M4 metalloprotease consists of the polypeptide of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11.

5. The method according to claim 1, wherein the M4 metalloprotease is added to the mash or to the wort.

6. The method according to claim 1, further comprising adding an alpha amylase to the mash.

7. The method according to claim 1, further comprising adding a beta glucanase to the mash.

8. The method according to claim 1, further comprising adding a pullulanase to the mash.

9. The method according to claim 1, further comprising adding a xylanase To the mash.

10. The method according to claim 1, further comprising adding a lipase to the mash.

11. The method according to claim 1, wherein the M4 metalloprotease is added in an amount of 1-100 mg enzyme protein per kg grist.

12. The method according to claim 1, wherein the grist comprises at least 10% (w/w) adjunct.

13. The method according to claim 1, wherein the adjunct is selected from the group consisting of barley, rice, corn, wheat, sorghum and cassava.

14. The method according to claim 1, further comprising fermenting the wort to obtain a beer.

15. The method according to claim 1, wherein the mashing is done in the absence of a protein rest.

16. The method according to claim 1, wherein the amount of free amino nitrogen (FAN) is increased by at least 20% when the protease according to the invention is added in an amount of 10 mg Enzyme Protein per kg grist as compared to a wort produced in the absence of the M4 metalloprotease.

* * * * *

SEQUENCE LISTING

```
<160> NUMBER OF SEQ ID NOS: 23

<210> SEQ ID NO 1
<211> LENGTH: 513
<212> TYPE: PRT
<213> ORGANISM: Micromonospora sp.61168

<400> SEQUENCE: 1

Met Arg Arg Thr Pro Leu Met Ser Gly Leu Ala Thr Ala Ala Leu Leu
1               5                   10                  15
```

-continued

```
Ala Thr Val Val Thr Val Pro Thr Ala Ala Thr Ala Ala Pro Thr Gly
         20                  25                  30

Thr Ala Asp Pro Phe Thr Arg Ala Val Ala Gln Leu Lys Ala His Ser
         35                  40                  45

Gly Ala Gly Leu Ala Ala Asp Gly Gln Thr Phe Thr Pro Arg Asn Val
    50                  55                  60

Val Thr Asp Ala Asp Gly Thr Glu His Val Arg Leu Asn Arg Tyr Ser
65                  70                  75                  80

Asp Gly Leu Pro Val Leu Gly Gly Asp Leu Val Val His Leu Gly Lys
                85                  90                  95

Gly Asp Ser Trp Arg Gly Ala Thr His Arg Leu Ala Asn Ala Pro Gln
             100                 105                 110

Arg Ala Pro Lys Ala Lys Leu Ser Glu Ala Ala Ser Lys Ile Ala
             115                 120                 125

Tyr Ala Ala Ser Thr Ala Thr Gly Arg Ser Val Ala Gly Ala Gln Leu
    130                 135                 140

Val Phe Asp Ala Gly Asp Thr Ala Thr Thr Leu Ala Tyr Glu Val Val
145                 150                 155                 160

Val Gly Gly Thr His Ala Asp Gly Thr Pro Ser Glu Leu His Val Leu
                165                 170                 175

Val Asp Ala Thr Thr Gly Ala Val Arg Asp Ser Trp Glu Gly Val Gln
             180                 185                 190

Arg Glu Gly Thr Gly Asn Thr Phe His Ser Gly Thr Val Ser Val Gly
             195                 200                 205

Ser Asn Leu Ser Gly Ser Thr Tyr Gln Leu Ala Asp Pro Ala Arg Gly
    210                 215                 220

Asn His Arg Thr Tyr Asp Leu Asn Gly Arg Thr Ser Gly Thr Gly Thr
225                 230                 235                 240

Leu Val Thr Ser Thr Asn Asn Val Phe Gly Asn Gly Thr Leu Thr Asn
                245                 250                 255

Arg Gln Thr Ala Ala Asp Ala Ala Phe Gly Ala Gln Lys Thr Trp
             260                 265                 270

Asp Tyr Tyr Lys Ser Ala His Gly Arg Asn Gly Ile Arg Asn Asp Gly
             275                 280                 285

Val Gly Ala Tyr Ser Arg Val His Tyr Ser Ser Asn Tyr Ala Asn Ala
    290                 295                 300

Phe Trp Gln Asp Ala Cys Phe Cys Met Thr Tyr Gly Asp Gly Gly Ser
305                 310                 315                 320

Gly Trp Tyr Pro Leu Thr Ser Leu Asp Val Ala Gly His Glu Met Thr
                325                 330                 335

His Gly Val Thr Ser Asn Thr Ala Gly Leu Arg Tyr Ser Gly Glu Ser
             340                 345                 350

Gly Gly Leu Asn Glu Ala Thr Ser Asp Ile Phe Gly Thr Leu Val Glu
             355                 360                 365

Phe Tyr Ala Ala Ser Ala Lys Asp Pro Gly Asp Tyr Leu Ile Gly Glu
    370                 375                 380

Lys Leu Arg Ser Thr Gly Thr Pro Leu Arg Tyr Met Asp Lys Pro Ser
385                 390                 395                 400

Lys Asp Gly Lys Ser Ala Asp Cys Trp Ser Ser Val Gly Gly Leu
                405                 410                 415

Asp Val His Tyr Ser Ser Gly Val Ala Asn His Phe Tyr Leu Leu
             420                 425                 430
```

```
Ala Val Gly Ser Gly Thr Ser Ser Tyr Gly Thr Ser Thr Cys Asn
            435                 440                 445

Gly Thr Thr Ile Thr Gly Ile Gly Asn Thr Lys Ala Gly Ala Ile Trp
450                 455                 460

Tyr Arg Ala Leu Thr Arg Tyr Met Thr Thr Thr Asn Tyr Lys Gly
465                 470                 475                 480

Ala Arg Thr Ala Thr Leu Ser Ala Ala Thr Asp Leu Tyr Gly Ala Thr
                    485                 490                 495

Ser Thr Glu Tyr Lys Thr Val Ala Ala Ala Trp Ala Ala Val Ser Val
                500                 505                 510

Ser

<210> SEQ ID NO 2
<211> LENGTH: 552
<212> TYPE: PRT
<213> ORGANISM: Streptomyces thermoalcalitolerans

<400> SEQUENCE: 2

Met Thr Pro Arg Tyr Ala Arg Pro Arg Arg Thr Ala Leu Ala Leu Ala
1               5                   10                  15

Thr Ala Val Val Ala Gly Ala Leu Leu Gly Thr Gly Leu Ser Thr Gly
                20                  25                  30

Ala Ser Ala Gln Pro Gln Ala Gly Ser Thr Gly Ala Ala Pro Leu Ala
            35                  40                  45

Ala Ala Pro Val Leu Leu Ser Asp Ala Glu Arg Thr Ser Leu Ile Gln
        50                  55                  60

Gln Ala Gln Ala Asp Ala Val Gly Thr Ala Arg Glu Ile Gly Leu Gly
65                  70                  75                  80

Ala Gln Glu Lys Leu Val Val Arg Asp Val Lys Asp Ala Asp Gly
                85                  90                  95

Thr Val His Thr Arg Tyr Glu Arg Thr Tyr Ala Gly Leu Pro Val Leu
            100                 105                 110

Gly Gly Asp Leu Ile Val His Thr Ser Arg Thr Gly Arg Thr Gln Gly
        115                 120                 125

Val Thr Lys Ala Thr Glu Ala Thr Ile Lys Val Asp Thr Leu Thr Pro
130                 135                 140

Arg Ile Ala Ala Ala Lys Ala Glu Lys Gln Ala Val Thr Leu Ala Arg
145                 150                 155                 160

Ala Ala Gly Ser Glu Asn Thr Thr Pro Asp Gln Ala Pro Arg Lys Val
                165                 170                 175

Ile Trp Ala Gly Asp Gly Thr Pro Val Leu Ala Tyr Glu Thr Val Val
            180                 185                 190

Gly Gly Leu Gln Asp Asp Gly Thr Pro Asn Glu Leu His Val Ile Thr
        195                 200                 205

Asp Ala Thr Thr Gly Glu Lys Leu Tyr Glu Tyr Gln Gly Val Val Asn
210                 215                 220

Gly Thr Gly Arg Thr Leu Tyr Ser Gly Thr Val Thr Leu Ser Thr Thr
225                 230                 235                 240

Arg Ser Gly Ser Thr Tyr Gln Leu Tyr Asp Thr Thr Arg Gly Gly His
                245                 250                 255

Arg Thr Tyr Asn Leu Ala Arg Gly Thr Ser Gly Thr Gly Thr Leu Phe
            260                 265                 270

Thr Asp Ala Asp Asp Val Trp Gly Thr Gly Thr Ala Ser Ser Ser Ser
        275                 280                 285
```

```
Ser Asp Gln Thr Ala Ala Asp Ala Ala Tyr Gly Ala Gln Val Thr
    290                 295                 300

Trp Asp Phe Tyr Lys Asn Val Phe Gly Arg Asn Gly Ile Arg Asn Asn
305                 310                 315                 320

Gly Thr Ala Ala Tyr Ser Arg Val His Tyr Gly Asn Asn Tyr Ile Asn
                325                 330                 335

Ala Phe Trp Ser Asp Ser Cys Phe Cys Met Thr Tyr Gly Asp Gly Ala
            340                 345                 350

Gly Asn Val Lys Pro Leu Thr Ser Leu Asp Val Ala Gly His Glu Met
                355                 360                 365

Ser His Gly Leu Thr Ser Tyr Thr Ala Gly Leu Arg Tyr Ser Gly Glu
    370                 375                 380

Ser Gly Gly Leu Asn Glu Ala Thr Ser Asp Ile Phe Gly Thr Gly Val
385                 390                 395                 400

Glu Phe Tyr Ala Asn Asn Ala Ser Asp Pro Gly Asp Tyr Leu Ile Gly
                405                 410                 415

Glu Lys Ile Asp Ile Asn Gly Asn Gly Thr Pro Leu Arg Tyr Met Asp
            420                 425                 430

Arg Pro Ser Lys Asp Gly Ala Ser Ala Asp Tyr Trp Ser Ser Gly Val
                435                 440                 445

Gly Asn Arg Asp Val His Tyr Ser Ser Gly Val Ala Asn His Phe Phe
    450                 455                 460

Tyr Leu Leu Ala Glu Gly Ser Gly Ala Lys Thr Ile Asn Gly Val Ser
465                 470                 475                 480

Tyr Asn Ser Pro Thr Tyr Asp Gly Ser Arg Ile Thr Gly Ile Gly Arg
                485                 490                 495

Asp Lys Ala Leu Gln Ile Trp Tyr Lys Ala Leu Thr Thr Tyr Met Thr
            500                 505                 510

Ser Thr Thr Thr Tyr Lys Gly Ala Arg Thr Ala Thr Leu Asn Ala Ala
                515                 520                 525

Ala Ala Leu Tyr Gly Ser Gly Ser Thr Glu Tyr Asn Thr Val Ala Ala
    530                 535                 540

Ala Trp Thr Ala Val Asn Val Thr
545                 550

<210> SEQ ID NO 3
<211> LENGTH: 552
<212> TYPE: PRT
<213> ORGANISM: Streptomyces ginsengisoli

<400> SEQUENCE: 3

Met Thr Pro Arg Tyr Ala Arg His Lys Arg Ile Thr Leu Ala Val Ala
1               5                   10                  15

Thr Ala Val Ala Ala Gly Ala Leu Leu Ser Thr Gly Leu Thr Thr Ser
                20                  25                  30

Ala Ser Ala Gln Thr Thr Ala Glu Ser Thr Gly Ala Ala His Leu Ala
            35                  40                  45

Ala Ala Pro Thr Phe Leu Thr Asn Ala Ala Arg Thr Ser Leu Ile Gln
        50                  55                  60

Gln Ala Gln Ala Asp Ala Ser Gly Thr Ala Gln Glu Ile Gly Leu Gly
65                  70                  75                  80

Ala Lys Glu Glu Leu Val Ala Arg Asp Val Ile Gln Asp Ala Asp Gly
                85                  90                  95

Thr Val His Thr Arg Tyr Glu Arg Thr Tyr Ala Gly Leu Pro Val Leu
            100                 105                 110
```

```
Gly Gly Asp Leu Ile Val His Ser Ser Lys Ala Gly Lys Thr Gln Gly
            115                 120                 125
Val Thr Arg Ala Asn Lys Ala Ile Lys Val Ala Thr Leu Thr Pro
130                 135                 140
Lys Val Ala Thr Ala Lys Ala Glu Lys Gln Ala Val Thr Leu Ala Gln
145                 150                 155                 160
Ala Ala Gly Ser Glu Lys Val Thr Ala Asp Gln Ala Pro Arg Lys Val
                165                 170                 175
Ile Trp Ala Gly Asp Gly Thr Pro Val Leu Ala Tyr Glu Thr Val Val
                180                 185                 190
Gly Gly Leu Gln Glu Asp Gly Thr Pro Asn Gln Leu His Val Ile Thr
            195                 200                 205
Asp Ala Ala Thr Gly Gln Lys Leu Tyr Glu Tyr Gln Gly Ile Glu Thr
210                 215                 220
Gly Thr Gly Lys Thr Leu Tyr Ser Gly Thr Val Ser Leu Thr Thr Thr
225                 230                 235                 240
Leu Ser Gly Ser Thr Tyr Gln Leu Tyr Asp Thr Thr Arg Gly Gly His
                245                 250                 255
Lys Thr Asn Asn Leu Ala Gly Lys Thr Ser Gly Thr Gly Thr Leu Phe
            260                 265                 270
Thr Asn Thr Thr Asp Val Trp Gly Thr Gly Thr Ala Ser Ser Ser Thr
            275                 280                 285
Thr Asp Gln Thr Ala Ala Ala Asp Ala Ala Tyr Gly Ala Gln Thr Thr
            290                 295                 300
Trp Asp Phe Tyr Lys Asn Thr Phe Gly Arg Asn Gly Ile Lys Asn Asn
305                 310                 315                 320
Gly Val Gly Ala Tyr Ser Arg Val His Tyr Gly Asn Asn Tyr Val Asn
                325                 330                 335
Ala Phe Trp Asp Asp Ser Cys Phe Cys Met Thr Tyr Gly Asp Gly Ser
            340                 345                 350
Gly Asn Thr His Pro Leu Thr Ser Leu Asp Val Ala Gly His Glu Met
            355                 360                 365
Ser His Gly Val Thr Ala Ala Thr Ala Lys Leu Asn Tyr Ser Gly Glu
            370                 375                 380
Ser Gly Gly Leu Asn Glu Ala Thr Ser Asp Ile Phe Gly Thr Gly Val
385                 390                 395                 400
Glu Phe Tyr Ala Asn Asn Ala Ser Asp Pro Gly Asp Tyr Leu Ile Gly
                405                 410                 415
Glu Lys Ile Asn Ile Asn Gly Asn Gly Thr Pro Leu Arg Tyr Met Asp
            420                 425                 430
Lys Pro Ser Lys Asp Gly Gly Ser Ala Asp Tyr Trp Ser Ser Thr Val
            435                 440                 445
Gly Ser Lys Asp Val His Tyr Ser Ser Gly Val Gly Asn His Phe Phe
450                 455                 460
Tyr Leu Leu Ala Glu Gly Ser Gly Ala Lys Thr Ile Asn Gly Val Ser
465                 470                 475                 480
Tyr Asn Ser Pro Thr Tyr Asn Gly Ala Thr Val Thr Gly Ile Gly Arg
                485                 490                 495
Ala Lys Ala Leu Gln Ile Trp Tyr Lys Ala Leu Thr Thr Tyr Met Thr
            500                 505                 510
Ser Thr Thr Asn Tyr Lys Ala Ala Arg Thr Ala Thr Leu Asn Ala Ala
            515                 520                 525
```

Ser Ala Leu Tyr Gly Ser Gly Ser Thr Glu Tyr Asn Thr Val Ala Ala
530                 535                 540

Ala Trp Thr Ala Val Asn Val Thr
545                 550

<210> SEQ ID NO 4
<211> LENGTH: 680
<212> TYPE: PRT
<213> ORGANISM: Kribbella aluminosa

<400> SEQUENCE: 4

Met Ala Val Val Ala Ala Gly Leu Ala Thr Thr Phe Thr Ala Ser
1               5                   10                  15

Thr Ala Gly Ala Ala Asp Arg Thr Ala Pro Leu Pro Gly Phe Asn Gln
                20                  25                  30

Pro Ala Ala Val Gln Ala Glu Gln Ala Leu Thr Ala Arg Thr Ala Ala
                35                  40                  45

Ala Leu Gly Leu Gly Thr Gly Glu Gln Leu Lys Val Arg Asp Val Val
            50                  55                  60

Lys Asp Pro Asp Gly Thr Glu Tyr Val Arg Tyr Asp Arg Thr Phe Asn
65                  70                  75                  80

Gly Leu Lys Val Val Gly Gly Asp Leu Ile Val Lys Arg Lys Gly Glu
                85                  90                  95

Ser Ile Gly Gln Val Thr Tyr Asn Arg Gly Ala Lys Ala Val Ala Val
                100                 105                 110

Ala Thr Lys Pro Thr Leu Ser Gln Ser Ala Ala Leu Ala Lys Gly Ala
            115                 120                 125

Gln Ala Ala Glu Phe Lys Ala Thr Gly Asn Lys Gly Glu Leu Val Val
        130                 135                 140

Phe Val Thr Pro Thr Lys Pro Val Leu Ala Tyr Glu Val Val Thr Thr
145                 150                 155                 160

Gly Val Lys Ala Asp Gln Thr Pro Ser Val Leu His Ser Phe Ile Asp
                165                 170                 175

Ala Lys Thr Gly Ala Val Leu Asp Gln Asp Asp Glu Val Lys Thr Gly
                180                 185                 190

Thr Gly Asn Ser Met Tyr Ser Gly Thr Val Ser Ile Gly Thr Ser Gly
            195                 200                 205

Ser Tyr Thr Met Ser Asp Pro Thr Arg Gly Gly Asn Tyr Thr Thr Asp
        210                 215                 220

Leu Asn Gly Ser Thr Ser Gly Ser Gly Thr Thr Phe Thr Asp Pro Asp
225                 230                 235                 240

Asp Thr Trp Gly Asn Gly Ser Thr Ser Arg Gln Thr Ala Gly Val
                245                 250                 255

Asp Ala His Tyr Gly Ala Gln Leu Thr Trp Asp Tyr Tyr Lys Asn Val
                260                 265                 270

His Gly Arg Asn Gly Ile Phe Asn Asn Gly Gln Gly Ala Arg Ser Arg
            275                 280                 285

Val His Tyr Gly Asn Ala Tyr Val Asn Ala Phe Trp Asp Gly Thr Gln
        290                 295                 300

Met Thr Tyr Gly Asp Gly Ala Ser Asn Ala Arg Pro Leu Thr Ser Ile
305                 310                 315                 320

Asp Val Ala Gly His Glu Met Ser His Gly Val Thr Glu Ala Thr Ala
                325                 330                 335

Asn Leu Asn Tyr Ser Gly Asp Ala Gly Gly Leu Asn Glu Ala Thr Ser
                340                 345                 350

```
Asp Ile Phe Gly Thr Ala Val Glu Phe Ser Ala Asn Asn Ser Ser Asp
            355                 360                 365

Pro Gly Asp Tyr Leu Ile Gly Glu Lys Ile Asn Ile Asn Gly Asn Gly
        370                 375                 380

Thr Pro Leu Arg Tyr Met Asp Lys Pro Ser Lys Asp Gly Arg Ser Val
385                 390                 395                 400

Asp Cys Trp Ser Thr Ser Thr Gly Gly Leu Asp Pro His Tyr Ser Ser
                405                 410                 415

Gly Pro Leu Asn His Trp Phe Tyr Leu Ala Ser Glu Gly Thr Gly Ser
            420                 425                 430

Lys Val Ile Gly Gly Val Thr His Ser Ser Thr Ala Cys Asn Gly Ala
        435                 440                 445

Thr Ile Thr Gly Val Gly Arg Asp Val Ala Ala Lys Val Trp Tyr Arg
    450                 455                 460

Thr Leu Ser Thr Lys Leu Ser Ser Gly Ser Thr Tyr Lys Asp Ala Arg
465                 470                 475                 480

Glu Gly Ala Ile Asn Ser Ala Lys Glu Leu Tyr Gly Ala Asp Ser Ala
                485                 490                 495

Gln Cys Lys Gly Ile Glu Ala Ala Phe Asn Gly Ile Ser Val Pro Ala
            500                 505                 510

Gly Ala Ala Cys Gly Gly Thr Asp Pro Glu Pro Thr Gly
        515                 520                 525

Gly Asn Leu Leu Lys Asn Pro Gly Phe Glu Ser Gly Ala Val Asp Trp
    530                 535                 540

Thr Gly Thr Ala Gly Pro Ile Thr Asn Asp Ser Gly Arg Pro Ala Arg
545                 550                 555                 560

Thr Gly Thr Trp Lys Leu Trp Leu Gly Gly Asn Gly Arg Thr Val Thr
                565                 570                 575

Glu Asn Val Gly Gln Ser Val Ala Ile Pro Ala Ser Ala Thr Ser Ala
            580                 585                 590

Thr Leu Ser Phe Trp Ile Arg Ile Asp Thr Ala Glu Thr Thr Ser Ser
        595                 600                 605

Thr Val Tyr Asp Arg Ala Leu Val Gln Ile Val Asp Gly Ser Thr Thr
    610                 615                 620

Thr Thr Leu Ala Thr Tyr Ser Asn Leu Asn Lys Asn Thr Ser Tyr Ile
625                 630                 635                 640

Gln Lys Thr Leu Asn Val Thr Ala Tyr Lys Gly Lys Thr Val Thr Val
                645                 650                 655

Lys Phe Val Gly Gln Glu Asp Ser Ser Leu Gln Thr Ser Phe Val Ile
            660                 665                 670

Asp Asp Thr Ser Leu Thr Ala Ser
        675                 680

<210> SEQ ID NO 5
<211> LENGTH: 679
<212> TYPE: PRT
<213> ORGANISM: Streptomyces sp-61982

<400> SEQUENCE: 5

Met Arg Ser Arg Ser Ser Arg Arg Thr Pro His Thr Pro Ala His
1               5                   10                  15

Arg Ala Ala Ala Val Ala Leu Val Gly Val Ser Ala Leu Leu Ala Ala
                20                  25                  30

Ala Val Gln Ser Gly Ala Ala Ser Ala Thr Pro Thr Glu Ala Thr Val
```

```
                  35                  40                  45
Gly Lys Thr Asn Leu Ala His Val Ala Ala Lys Leu Thr Pro Ser Gln
 50                  55                  60

Arg Ala Glu Leu Ile Arg Asp Ala Asp Gly Lys Ala Arg Thr Ala
 65                  70                  75                  80

Lys Asp Leu Gly Leu Gly Ala Gln Glu Lys Leu Val Val Lys Asp Val
                     85                  90                  95

Ile Lys Asp Ala Asp Gly Thr Leu His Thr Arg Tyr Glu Arg Thr Tyr
                    100                 105                 110

Ala Gly Leu Pro Val Leu Gly Gly Asp Leu Ile Val Asp Thr Ala Lys
                    115                 120                 125

Ser Gly Gln Thr Glu Arg Val Leu Lys Ala Thr Asn Ala Thr Val Lys
                    130                 135                 140

Val Ala Ser Leu Thr Pro Arg Val Ser Lys Ala Thr Ala Glu Gln Gln
145                 150                 155                 160

Ala Val Gln Arg Ala Lys Ala Leu Gly Ser Thr Lys Ala Val Glu Gln
                    165                 170                 175

Ser Ser Arg Lys Val Val Trp Ala Ala Ser Gly Lys Pro Val Leu Ala
                    180                 185                 190

Tyr Glu Thr Val Ile Gly Gly Phe Gln Asp Asp Gly Thr Pro Asn Ala
                    195                 200                 205

Leu His Val Ile Thr Asp Ala Ser Thr Gly Lys Glu Leu Phe Arg His
                    210                 215                 220

Gln Gly Ile Glu Thr Gly Ile Gly Asn Thr Gln Tyr Ser Gly Gln Val
225                 230                 235                 240

Thr Leu Thr Thr Thr Gln Ser Gly Ser Thr Tyr Thr Leu Asn Asp Gly
                    245                 250                 255

Ala Arg Gly Gly His Lys Thr Tyr Asn Leu Asn His Gly Ser Ser Gly
                    260                 265                 270

Thr Gly Thr Leu Phe Ser Gln Ser Ser Asp Thr Trp Gly Asn Gly Thr
                    275                 280                 285

Thr Ser Asn Ala Ala Thr Ala Gly Ala Asp Ala His Tyr Gly Ala Gln
                    290                 295                 300

Glu Thr Trp Asp Phe Tyr Lys Asn Thr Phe Gly Arg Asn Gly Ile Lys
305                 310                 315                 320

Asn Asp Gly Thr Ala Ala Tyr Ser Arg Val His Tyr Gly Asn Ser Tyr
                    325                 330                 335

Val Asn Ala Phe Trp Asp Asp Ser Cys Phe Cys Met Thr Tyr Gly Asp
                    340                 345                 350

Gly Ser Gly Asn Ala Asp Pro Leu Thr Ser Leu Asp Val Ala Gly His
                    355                 360                 365

Glu Met Ser His Gly Val Thr Ser Asn Thr Ala Gly Leu Asp Tyr Ser
                    370                 375                 380

Gly Glu Ser Gly Gly Leu Asn Glu Ala Thr Ser Asp Ile Met Gly Thr
385                 390                 395                 400

Gly Val Glu Phe Tyr Ala Asn Asn Ser Thr Asp Val Gly Asp Tyr Leu
                    405                 410                 415

Ile Gly Glu Lys Ile Asn Ile Asn Gly Asp Gly Thr Pro Leu Arg Tyr
                    420                 425                 430

Met Asp Lys Pro Ser Lys Asp Gly Gly Ser Ala Asp Ser Trp Ser Ser
                    435                 440                 445

Gly Val Gly Asn Leu Asp Val His Tyr Ser Ser Gly Val Ala Asn His
                    450                 455                 460
```

```
Phe Phe Tyr Leu Leu Ser Glu Gly Ser Gly Ala Lys Val Ile Asn Gly
465                 470                 475                 480

Val Ser Tyr Asn Ser Pro Thr Ala Asp Gly Leu Pro Val Thr Gly Ile
                485                 490                 495

Gly Arg Asp Lys Ala Leu Gln Ile Trp Tyr Arg Ala Leu Thr Thr Lys
            500                 505                 510

Phe Thr Ser Thr Thr Asn Tyr Ala Gly Ala Arg Thr Gly Thr Leu Ala
        515                 520                 525

Ala Ala Gly Glu Leu Tyr Gly Thr Ser Ser Ala Glu Tyr Lys Ala Val
    530                 535                 540

Gln Asp Ala Trp Ala Ala Val Ala Val Gly Ser Arg Ser Gly Gly Gly
545                 550                 555                 560

Ser Gly Gly Gly Thr Ser Tyr Glu Asn Thr Ser Pro Val Ser Ile Pro
                565                 570                 575

Asp Asn Gly Pro Ala Val Thr Ser Ser Ile Thr Val Ser Gly Arg Thr
            580                 585                 590

Gly Asn Ala Pro Ser Ser Leu Gln Val Gly Val Asp Ile Thr His Thr
        595                 600                 605

Trp Arg Gly Asp Leu Val Ile Asp Leu Val Gly Pro Ser Gly Thr Ser
    610                 615                 620

Tyr Arg Leu Lys Asn Phe Ser Ser Asp Ser Ala Asp Val Lys
625                 630                 635                 640

Glu Thr Tyr Thr Val Asn Ala Ser Ser Glu Thr Ala Asn Gly Thr Trp
                645                 650                 655

Lys Leu Lys Val Gln Asp Gln Ala Gln Asp Val Gly Thr Leu Asn
            660                 665                 670

Ser Trp Lys Leu Thr Phe Pro
        675

<210> SEQ ID NO 6
<211> LENGTH: 509
<212> TYPE: PRT
<213> ORGANISM: Kribbella aluminosa

<400> SEQUENCE: 6

Met Lys Arg Ile His Arg Ala Gly Leu Ala Ala Thr Ala Ile Ala Gly
1               5                   10                  15

Leu Ala Val Ala Ser Ile Thr Ala Thr Val Gln Ala Ala Gln Pro Gly
                20                  25                  30

Ser Gly Pro Ala Val Ser Pro Val Ala Ala Arg Ala Asn Ala Ala
            35                  40                  45

Gln Leu Gly Leu Gly Asp Ala Gly Asp Met Val Val Arg Asp Val Val
    50                  55                  60

Thr Asp Gly Asp Gly Ser Thr His Val Arg Phe Asp Arg Thr Tyr Gln
65                  70                  75                  80

Gly Leu Pro Val Val Gly Gly Asp Val Val His Gln Asp Lys Ala
                85                  90                  95

Gly Lys Ala Arg Ser Ser Ser Gly Val Gly Lys Leu Ser Leu Ser
            100                 105                 110

Thr Lys Pro Thr Ala Ser Ala Ala Thr Ala Phe Ala Ala Ala Lys Thr
        115                 120                 125

Lys Ser Ser Lys Gln Gln Leu Val Val Phe Val Thr Asn Ala Gly Gln
    130                 135                 140

Ala Lys Leu Ala Tyr Lys Val Val Ser Glu Gly Arg Lys Ala Asn Gly
```

-continued

```
            145                 150                 155                 160
Glu Pro Thr Gly Thr Glu Thr Tyr Val Asp Ala Gln Thr Gly Lys Val
                165                 170                 175

Leu Asp Ser Trp Thr Thr Val His Glu Asp Leu Gly Ser Gly Thr Gly
            180                 185                 190

Leu Tyr Val Gly Thr Val Gly Leu Asp Thr Thr Lys Ser Gly Thr Gly
                195                 200                 205

Trp Thr Met Val Asp Pro Val Arg Gly Gly Asn Ala Thr Tyr Asn Ala
    210                 215                 220

Gly Thr Leu Phe Ser Asp Ala Asp Asn Val Trp Gly Ser Gly Ser Asn
225                 230                 235                 240

Ser Asn Pro Gln Ser Ala Gly Val Asp Ala His Tyr Gly Ile Ala Glu
                245                 250                 255

Thr Trp Asp Tyr Tyr Lys Asn Val His Ser Arg Asn Gly Ile Ala Asn
                260                 265                 270

Asp Gly Lys Gly Ala Lys Ser Tyr Val His Asp Gly Ala Tyr Val Asn
                275                 280                 285

Ala Ser Trp Ser Asp Ser Cys Phe Cys Met Arg Tyr Gly Asp Gly Asp
    290                 295                 300

Pro Ser Gln Gly Ile Gly Pro Leu Val Glu Leu Asp Ile Ala Gly His
305                 310                 315                 320

Glu Met Ser His Gly Val Thr Ser Arg Ser Ala Gly Leu Arg Tyr Ser
                325                 330                 335

Gly Glu Ser Gly Gly Leu Asn Glu Ser Thr Ser Asp Ile Phe Gly Thr
                340                 345                 350

Ala Val Glu Trp Tyr Ala Asn Asn Ser Gln Asp Ala Pro Asp Tyr Val
                355                 360                 365

Met Gly Glu Glu Ile Phe Thr Asp Tyr Asn Pro Ala Val Asn Tyr Ile
    370                 375                 380

Arg Arg Met Asp Lys Pro Ser Met Asp Gly Ala Ser Ala Asp Ser Trp
385                 390                 395                 400

Ser Arg Ser Val Gly Arg Leu Asn Val His Tyr Ser Ser Gly Val Gly
                405                 410                 415

Asn His Phe Phe Tyr Leu Leu Ser Glu Gly Ser Gly Ala Lys Thr Ile
                420                 425                 430

Asn Gly Val Ala Tyr Asn Ser Pro Thr Ala Asn Gly Val Thr Val Thr
                435                 440                 445

Gly Ile Gly Ile Thr Lys Ala Glu Lys Ile Trp Tyr Arg Ala Leu Thr
    450                 455                 460

Thr Tyr Met Thr Ser Arg Thr Asp Tyr His Gly Ala Arg Thr Ala Thr
465                 470                 475                 480

Leu Asn Ala Ala Thr Asp Leu Tyr Gly Ala Ser Ser Pro Glu Arg Ala
                485                 490                 495

Ala Val Asp Lys Ala Trp Ala Val Asn Val Leu Pro
                500                 505
```

<210> SEQ ID NO 7
<211> LENGTH: 673
<212> TYPE: PRT
<213> ORGANISM: Streptomyces champavatii

<400> SEQUENCE: 7

```
Met Arg Pro Thr Ser His Arg Arg Ala Val Ala Gly Gly Ala Leu Ala
1               5                   10                  15
```

```
Ala Val Thr Ala Leu Leu Ala Val Thr Ala Thr Ala Pro Ala Thr
            20                  25                  30

Ala Ala Asp Pro Ala Pro Ala Ala Lys Pro Thr Ala Ala Arg Thr Gly
        35                  40                  45

Ala Leu Pro Ala Asp Leu Ser Pro Ala Gln Arg Ala Ala Leu Ile Arg
 50                  55                  60

Ala Ala Glu Ala Lys Thr Ala Ser Val Ala Ala Glu Leu Gly Leu Gly
 65                  70                  75                  80

Ala Gln Glu Lys Leu Leu Val Arg Asp Val Val Lys Asp Arg Asp Gly
                85                  90                  95

Thr Leu His Thr Arg Tyr Glu Arg Thr Trp Ser Gly Leu Pro Val Leu
            100                 105                 110

Gly Gly Asp Leu Val Val Ala Ala Glu Pro Asp Gly Thr Pro Ala Thr
        115                 120                 125

Val Thr Lys Ala Ser Arg Asn Ala Leu Lys Gly Ile Ala Thr Lys Ala
130                 135                 140

Glu Ile Ala Pro Ser Ala Ala Lys Lys Gln Ala Leu Asn Ala Ala Glu
145                 150                 155                 160

Ala His Asp Ala Glu Lys Ala Ala Thr Asp Gly Ala Pro Arg Gln Val
                165                 170                 175

Val Trp Asn Ala Asp Gly Lys Pro Val Leu Ala Phe Glu Thr Val Val
            180                 185                 190

Gly Gly Leu Gln His Asp Gly Thr Pro Asn Glu Leu His Val Val Thr
        195                 200                 205

Asp Ala Ala Thr Gly Glu Lys Leu His Glu Trp Gln Ala Val Glu Asn
210                 215                 220

Gly Thr Gly Asn Thr Gln Tyr Ser Gly Thr Val Thr Leu Gly Ser Thr
225                 230                 235                 240

Lys Ser Gly Ser Thr Trp Asn Leu Thr Asp Ala Gly Arg Gly Asn His
                245                 250                 255

Arg Thr Asn Asn Leu Asn Arg Ser Thr Ser Gly Thr Gly Thr Leu Phe
            260                 265                 270

Ser Gly Pro Asp Asp Val Trp Gly Asn Gly Leu Ala Ser Asn Thr Glu
        275                 280                 285

Thr Ala Ala Asp Ala Ala Tyr Gly Ala Gln Ala Thr Trp Asp Tyr
290                 295                 300

Tyr Lys Asp Val His Gly Arg Ser Gly Ile Arg Gly Asp Gly Val Gly
305                 310                 315                 320

Ala Tyr Ser Arg Val His Tyr Gly Asn Asn Tyr Val Asn Ala Phe Trp
                325                 330                 335

Thr Asp Ser Cys Phe Cys Met Thr Tyr Gly Asp Gly Ala Gly Asn Ala
            340                 345                 350

Ala Pro Leu Thr Ser Leu Asp Val Ala Ala His Glu Met Thr His Gly
        355                 360                 365

Leu Thr Ser Val Thr Ala Lys Leu Val Tyr Ser Gly Glu Ser Gly Gly
370                 375                 380

Leu Asn Glu Ala Thr Ser Asp Ile Leu Ala Ala Val Glu Phe His
385                 390                 395                 400

Glu Asn Asn Ala Ala Asp Lys Gly Asp Tyr Leu Ile Gly Glu Lys Ile
                405                 410                 415

Asp Ile Asn Gly Asn Gly Thr Pro Leu Arg Tyr Met Asp Lys Pro Ser
            420                 425                 430

Arg Asp Gly Lys Ser Lys Asp Ser Trp Tyr Ser Gly Ile Gly Ser Val
```

```
                435                 440                 445
Asp Val His Tyr Ser Ser Gly Pro Ala Asn His Phe Phe Tyr Leu Leu
        450                 455                 460
Ser Glu Gly Ser Gly Ala Lys Thr Val Asn Gly Val Ser Tyr Asp Ser
465                 470                 475                 480
Pro Thr Ala Asp Gly Leu Pro Val Thr Gly Ile Gly Arg Asp Lys Ala
                485                 490                 495
Ala Leu Ile Trp Phe Lys Ala Leu Thr Thr Lys Phe Thr Ser Thr Thr
            500                 505                 510
Asn Tyr Ala Gly Ala Arg Thr Gly Thr Leu Ala Val Ala Gly Glu Leu
            515                 520                 525
Tyr Gly Thr Ser Ser Ala Glu Tyr Lys Ala Val Gln Asp Ala Trp Ala
        530                 535                 540
Gly Val Ala Val Gly Ala Arg Ser Gly Gly Ser Gly Gly Thr Thr
545                 550                 555                 560
Phe Glu Asn Thr Thr Ala Val Ala Ile Pro Asp Ala Gly Ala Ala Val
                565                 570                 575
Thr Ser Asp Ile Thr Val Thr Gly Arg Thr Gly Asn Ala Pro Ala Ala
            580                 585                 590
Leu Gln Val Thr Val Asp Ile Ser His Thr Trp Arg Gly Asp Leu Val
            595                 600                 605
Ile Asp Leu Val Gly Pro Asn Gly Thr Ala Tyr Arg Leu Lys Asn Ala
        610                 615                 620
Ser Ser Ser Asp Ser Ala Asp Asn Val Gln Glu Thr Tyr Thr Val Asn
625                 630                 635                 640
Ala Ser Ala Gln Thr Ala Asn Gly Thr Trp Lys Leu Arg Val Gln Asp
                645                 650                 655
Thr Ala Arg Ser Asp Thr Gly Arg Ile Asn Ser Trp Lys Ile Val Leu
            660                 665                 670
Pro

<210> SEQ ID NO 8
<211> LENGTH: 549
<212> TYPE: PRT
<213> ORGANISM: Streptomyces kathirae

<400> SEQUENCE: 8

Met Ser Arg Ile Arg His Ile Arg Glu Ser Arg Leu Ala Ala Ala Gly
1               5                   10                  15
Thr Ala Ala Thr Thr Ala Ala Leu Leu Ala Ala Ala Leu Ala Pro Ala
            20                  25                  30
Pro Gly Ala Ala Ala Ala Asp Arg Pro Gly Arg Ala Thr Ala Ile Ser
        35                  40                  45
Asn Ala Ala Ala Ala Leu Val His Gln Ala Thr Arg Leu Gly Leu Thr
    50                  55                  60
Ser Ala Gln Gly Thr Ser Val Arg Asp Val Val Asp Pro Asp Gly
65                  70                  75                  80
Ser Gln His Val Arg Tyr Asp Arg Thr Phe Arg Asp Ile Pro Val Leu
                85                  90                  95
Gly Gly Asp Phe Val Val His Leu Ala Pro Gly Gly Ser Phe Arg Ser
            100                 105                 110
Ala Asp Arg Ala Thr Glu Arg Ala Ile Ser Val Pro Thr Thr Thr Pro
        115                 120                 125
Thr Val Lys Ala Pro Arg Ala Ala Asp Leu Ala Ala Ser Ala Leu Arg
```

```
                130             135             140
Ala Ala Asn Ala Gly Glu Leu Leu Lys Asn Val Thr Ala Lys Pro Gln
145                 150                 155                 160

Leu Val Val Asp Ala Leu His Gly Ala Pro Arg Leu Ala Trp Arg Thr
                165                 170                 175

Asn Ala Ala Gly Gln Asp Ser Leu Gly Asn Pro Val Ala Arg Thr Val
                180                 185                 190

Leu Thr Asp Ala Arg Thr Gly Lys Gln Ile Asp Ala Trp Asp Ser Ile
                195                 200                 205

Glu Thr Ala Thr Gly Asp Gly Lys Ser Leu Tyr Ser Gly Thr Val Pro
                210                 215                 220

Leu Gln Thr Thr Gln Ser Gly Ser Thr Tyr Gln Leu Lys Asp Pro Thr
225                 230                 235                 240

Arg Gly Asn Thr Tyr Thr Gly Asp Ala Ala Asn Lys Thr Asp Leu Cys
                245                 250                 255

Val Leu Ser Ile Cys Phe Ser Arg Ala Pro Ala Thr Leu Phe Thr Asp
                260                 265                 270

Ser Asp Asn His Trp Gly Thr Gly Thr Thr Ser Asp Arg Ser Ser Ala
                275                 280                 285

Ala Val Asp Ala Gln Tyr Gly Thr Asn Glu Thr Trp Asp Tyr Tyr Lys
                290                 295                 300

Asn Val His Gly Arg Asn Gly Ile Ala Gly Asp Gly Lys Gly Ser Tyr
305                 310                 315                 320

Asn Arg Val His Tyr Gly Thr Asp Tyr Asn Asn Ala Phe Trp Asp Asp
                325                 330                 335

Asn Cys Phe Cys Met Thr Tyr Gly Asp Gly Asp Gly Thr Thr Phe Gly
                340                 345                 350

Pro Leu Val Ala Leu Asp Val Ala Gly His Glu Met Ser His Gly Val
                355                 360                 365

Thr Ser Lys Thr Ala Ala Leu Thr Tyr Ser Gly Glu Ser Gly Gly Leu
                370                 375                 380

Asn Glu Ala Thr Ser Asp Val Phe Gly Thr Leu Val Glu Trp Tyr Ala
385                 390                 395                 400

Asn Ser Pro Ser Asp Pro Gly Asp Tyr Leu Ile Gly Glu Lys Ile Val
                405                 410                 415

Arg Ser Gly Phe Gly Lys Ser Ala Leu Arg Tyr Met Asp Lys Pro Ser
                420                 425                 430

Lys Asp Gly Asn Ser Ala Asp Cys Trp Ser Ser Val Gly Asn Leu
                435                 440                 445

Asp Val His Tyr Ser Ser Gly Val Ala Asn His Phe Ala Tyr Leu Leu
                450                 455                 460

Ala Glu Gly Ser Gly Ala Lys Thr Val Asn Gly Val Ala Tyr Asp Ser
465                 470                 475                 480

Pro Thr Cys Asn Gly Ser Thr Val Thr Gly Ile Gly Arg Asp Lys Leu
                485                 490                 495

Gly Lys Ile Trp Tyr Arg Ala Leu Thr Val Tyr Met Thr Ser Ser Thr
                500                 505                 510

Asn Tyr Ala Gly Ala Arg Thr Ala Thr Leu Ser Ala Ala Lys Asp Leu
                515                 520                 525

Tyr Gly Ala Gly Ser Thr Glu Tyr Asn Ala Val Ala Ala Ala Trp Ser
                530                 535                 540

Ala Val Asn Val Asn
545
```

<210> SEQ ID NO 9
<211> LENGTH: 667
<212> TYPE: PRT
<213> ORGANISM: Streptomyces kathirae

<400> SEQUENCE: 9

```
Met Arg Arg Ile Pro Arg Gln Ala Thr Ala Ala Gly Ala Leu Val Ala
1               5                   10                  15

Thr Ala Ala Phe Leu Ala Val Gly Met Gln Ala Ala Pro Ala Thr Ala
            20                  25                  30

Lys Pro Ala Pro His Ala Asp Ser Leu Arg Thr Gly Gly Leu Glu Ala
        35                  40                  45

Glu Leu Thr Gly Ala Gln His Thr Ala Leu Leu Gln Ser Ala Ala Arg
    50                  55                  60

Thr Thr Thr Gln Thr Ala Arg Ser Ile Gly Leu Gly Ser Lys Glu Lys
65                  70                  75                  80

Leu Val Val Lys Asp Val Val Lys Asp Asn Asp Gly Thr Leu His Thr
                85                  90                  95

Arg Tyr Glu Arg Thr Tyr Asp Gly Leu Pro Val Leu Gly Gly Asp Leu
            100                 105                 110

Ile Val His Thr Pro Pro Ala Ser Leu Ala Ala Gly Ala Val Ser Thr
        115                 120                 125

Thr Phe Asn Asn Lys His Ala Ile Lys Val Ala Thr Thr Ala Ala
    130                 135                 140

Phe Thr Lys Ser Ala Ala Glu Thr Lys Ala Leu Lys Ala Ala Lys Ala
145                 150                 155                 160

Leu Asp Ala Lys Lys Pro Ala Thr Asp Ser Ala Arg Lys Val Ile Trp
                165                 170                 175

Ala Gly Asn Gly Thr Pro Lys Leu Ala Trp Glu Thr Val Ile Gly Gly
            180                 185                 190

Phe Gln Asp Asp Gly Thr Pro Ser Gln Leu His Val Val Thr Asp Ala
        195                 200                 205

Thr Thr Gly Lys Glu Leu Tyr Arg Tyr Gln Gly Ile Lys Thr Gly Thr
    210                 215                 220

Gly Asn Thr Gln Tyr Ser Gly Thr Val Thr Leu Asn Thr Thr Leu Ser
225                 230                 235                 240

Gly Ser Thr Tyr Gln Leu Asn Asp Thr Thr Arg Gly Gly His Lys Thr
                245                 250                 255

Tyr Asn Leu Asn Asn Gly Thr Ser Gly Thr Gly Thr Leu Met Thr Asp
            260                 265                 270

Ser Asp Asp Val Trp Gly Asn Gly Ser Gly Ser Asn Ser Gln Thr Ala
        275                 280                 285

Gly Ala Asp Ala Ala Tyr Gly Ala Gln Met Thr Trp Asp Phe Tyr Lys
    290                 295                 300

Asn Thr Phe Gly Arg Ser Gly Ile Arg Asn Asp Gly Val Ala Ala Tyr
305                 310                 315                 320

Ser Arg Val His Tyr Ser Ser Ala Tyr Val Asn Ala Phe Trp Asp Asp
                325                 330                 335

Ser Cys Phe Cys Met Thr Tyr Gly Asp Gly Ser Gly Thr His Ala
            340                 345                 350

Leu Thr Ser Leu Asp Val Ala Gly His Glu Met Ser His Gly Val Thr
        355                 360                 365

Ser Asn Thr Ala Gly Leu Asn Tyr Thr Gly Glu Ser Gly Gly Leu Asn
```

```
                370             375             380
Glu Ala Thr Ser Asp Val Phe Gly Thr Gly Val Glu Phe Tyr Ala Asn
385                 390                 395                 400

Asn Ser Ser Asp Pro Gly Asp Tyr Leu Ile Gly Glu Lys Ile Asp Ile
            405                 410                 415

Asn Gly Asp Gly Thr Pro Leu Arg Tyr Met Asp Lys Pro Ser Lys Asp
            420                 425                 430

Gly Ala Ser Ala Asp Ser Trp Tyr Ser Gly Val Gly Asn Leu Asp Val
            435                 440                 445

His Tyr Ser Ser Gly Pro Ala Asn His Met Phe Tyr Leu Leu Ser Glu
            450                 455                 460

Gly Ser Gly Thr Lys Val Ile Asn Gly Val Thr Tyr Asn Ser Pro Thr
465                 470                 475                 480

Ser Asp Gly Val Ala Val Thr Gly Ile Gly Arg Ala Ala Ala Leu Gln
            485                 490                 495

Ile Trp Tyr Lys Ala Leu Thr Thr Tyr Met Thr Ser Ser Thr Asn Tyr
            500                 505                 510

Ala Ala Ala Arg Thr Ala Ala Leu Asn Ala Ala Ala Leu Tyr Gly
            515                 520                 525

Thr Asn Ser Thr Gln Tyr Ala Gly Val Gly Asn Ala Phe Ala Gly Ile
530                 535                 540

Asn Val Gly Gly His Ile Thr Pro Pro Ser Ser Gly Val Thr Val Thr
545                 550                 555                 560

Asn Pro Gly Ser Gln Ser Ser Thr Val Gly Thr Pro Val Ser Leu Gln
            565                 570                 575

Ile Ser Ala Ser Ser Thr Asn Ser Gly Ala Leu Thr Tyr Ser Ala Thr
            580                 585                 590

Gly Leu Pro Ala Gly Leu Ser Ile Asn Ser Ser Thr Gly Val Val Ser
            595                 600                 605

Gly Thr Pro Thr Thr Ala Gly Thr Tyr Ser Thr Val Thr Val Thr
            610                 615                 620

Asp Ser Thr Gly Ala Thr Gly Thr Ala Ser Phe Thr Trp Thr Val Ser
625                 630                 635                 640

Ser Ser Gly Gly Gly Thr Cys Thr Ser Arg Gln Leu Leu Gly Asn Pro
            645                 650                 655

Gly Phe Glu Ser Gly Asn Thr Thr Trp Thr Ala
            660                 665

<210> SEQ ID NO 10
<211> LENGTH: 549
<212> TYPE: PRT
<213> ORGANISM: Streptomyces sp-62237

<400> SEQUENCE: 10

Met Ser Pro Leu Tyr Ala Arg His Lys Arg Thr Thr Leu Ala Val Ala
1               5                   10                  15

Thr Ala Val Ala Ala Gly Ala Leu Leu Thr Thr Gly Leu Thr Thr Asn
            20                  25                  30

Ala Thr Ala Ala Ala Lys Gln Pro Leu Ala Ala Pro Thr Leu Leu
            35                  40                  45

Ser Asn Ser Ala Arg Thr Ala Leu Ile Gln Lys Ala Gln Ala Asp Val
        50                  55                  60

Ala Glu Thr Ala Gln Glu Ile Gly Leu Gly Ala Lys Glu Lys Leu Val
65                  70                  75                  80
```

-continued

```
Val Lys Asp Val Val Lys Asp Val Asp Gly Thr Val His Thr Arg Tyr
                85              90              95
Glu Arg Thr Tyr Ala Gly Leu Pro Val Leu Gly Gly Asp Leu Val Val
            100             105             110
His Thr Ser Lys Ser Gly Lys Ser Glu Gly Val Thr Arg Ala Thr Lys
        115             120             125
Ala Thr Ile Lys Val Ala Ser Leu Lys Pro Gly Ile Ser Thr Ala Lys
    130             135             140
Ala Glu Lys Thr Ala Leu Thr Ala Ala Lys Ala Leu Gly Ser Ala Lys
145             150             155             160
Ser Ala Ala Asp Gly Ala Arg Lys Val Ile Trp Ala Gly Ser Gly Thr
                165             170             175
Pro Val Leu Ala Tyr Glu Thr Val Val Gly Gly Phe Gln Asp Asp Gly
            180             185             190
Thr Pro Asn Gln Leu His Val Ile Thr Asp Ala Ala Thr Gly Lys Lys
        195             200             205
Leu Phe Glu Tyr Gln Gly Ile Glu Asn Ala Thr Gly Thr Gly Lys Thr
    210             215             220
Leu Tyr Ser Gly Thr Val Ser Leu Thr Thr Asn Leu Ser Gly Ser Thr
225             230             235             240
Tyr Gln Leu Tyr Asp Thr Thr Arg Gly Gly His Lys Thr Tyr Asn Leu
                245             250             255
Ser His Gly Thr Ser Ser Gly Thr Gly Thr Leu Phe Thr Asp Ala Asp
            260             265             270
Asn Val Trp Gly Thr Gly Ala Ala Ser Ser Ser Thr Asp Gln Thr
        275             280             285
Ala Ala Ala Asp Ala Ala Tyr Gly Ala Gln Glu Thr Trp Asp Phe Tyr
    290             295             300
Lys Asp Thr Phe Gly Arg Ser Gly Ile Lys Asn Asn Gly Val Gly Ala
305             310             315             320
Tyr Ser Arg Val His Tyr Gly Ser Ser Tyr Val Asn Ala Phe Trp Asp
                325             330             335
Asp Ser Cys Phe Cys Met Thr Tyr Gly Asp Gly Ser Ser Asn Thr His
            340             345             350
Pro Leu Thr Ser Leu Asp Val Ala Gly His Glu Met Ser His Gly Val
        355             360             365
Thr Ala Asn Thr Ala Gly Leu Asn Tyr Ser Gly Glu Ser Gly Gly Leu
    370             375             380
Asn Glu Ala Thr Ser Asp Ile Phe Gly Thr Gly Val Glu Phe Tyr Ala
385             390             395             400
Asn Asn Ser Ser Asp Val Gly Asp Tyr Leu Ile Gly Glu Lys Ile Asn
                405             410             415
Ile Asn Gly Asp Gly Thr Pro Leu Arg Tyr Leu Asp Lys Pro Ser Lys
            420             425             430
Asp Gly Ala Ser Ala Asp Tyr Trp Ser Ser Val Lys Asn Leu Asp
        435             440             445
Val His Tyr Ser Ser Gly Val Ala Asn His Phe Phe Tyr Leu Leu Ser
    450             455             460
Glu Gly Ser Gly Ser Lys Thr Ile Asn Gly Val Ser Tyr Asn Ser Pro
465             470             475             480
Thr Tyr Asn Ser Ser Thr Val Thr Gly Ile Gly Arg Ala Lys Ala Leu
                485             490             495
Gln Ile Trp Tyr Lys Ala Leu Thr Thr Tyr Phe Thr Ser Thr Thr Asn
```

```
            500                 505                 510
Tyr Lys Ser Ala Arg Thr Gly Thr Leu Ser Ala Ala Ala Leu Tyr
            515                 520                 525

Gly Ser Gly Ser Thr Glu Tyr Asn Ala Val Ala Ala Trp Thr Ala
            530                 535                 540

Val Asn Val Thr Ser
545
```

<210> SEQ ID NO 11
<211> LENGTH: 550
<212> TYPE: PRT
<213> ORGANISM: Streptomyces sp-61982

<400> SEQUENCE: 11

```
Met Ser Arg Ile Arg His Ala Arg Gly Ser Arg Leu Thr Ala Ala Gly
1               5                   10                  15

Thr Ala Thr Ala Ala Ala Leu Leu Gly Ala Ala Leu Ala Pro Ala
            20                  25                  30

Pro Thr Ala Gly Ala Ala Glu Gly Pro Ser Arg Ala Thr Ala Ile Ser
            35                  40                  45

Asn Ala Thr Ala Val Leu Asp Arg Leu Gly Ala Gln Leu Gly Leu Thr
50                  55                  60

Ala Ala Gln Gly Thr Ser Val Arg Asp Val Val Asp Pro Asp Gly
65                  70                  75                  80

Ser Gln His Val Arg Tyr Asp Arg Thr Tyr Arg Gln Leu Pro Val Leu
                85                  90                  95

Gly Gly Asp Phe Val Val His Leu Ala Pro Asp Gly Ser Tyr Arg Ser
            100                 105                 110

Thr Asp Arg Ala Thr Lys Arg Ser Val Ser Leu Ser Thr Ile Thr Pro
            115                 120                 125

Thr Val Arg Ala Pro Arg Ala Ala Asp Leu Ala Ala Thr Ala Leu Arg
            130                 135                 140

Ala Ala Asn Ala Gly Glu Leu Leu Lys Ser Val Thr Ala Lys Pro Gln
145                 150                 155                 160

Leu Val Val Asp Ala Thr His Gly Ala Pro Arg Leu Ala Trp Arg Thr
                165                 170                 175

Asp Ala Val Gly Lys Asp Ser Leu Gly Asn Pro Val Ala Arg Thr Val
            180                 185                 190

Val Thr Asp Ala Leu Thr Gly Arg Gln Ile Asp Ala Trp Asp Ser Ile
            195                 200                 205

Glu Thr Ala Thr Gly Asp Gly Lys Ser Leu Tyr Ser Gly Thr Val Pro
            210                 215                 220

Leu Gln Thr Thr Gln Ser Gly Ser Thr Tyr Gln Leu Lys Asp Pro Thr
225                 230                 235                 240

Arg Gly Asn Thr Tyr Thr Gly Asp Ala Ala Asn Gln Thr Asp Leu Cys
                245                 250                 255

Phe Leu Thr Ser Val Cys Val Ser Arg Ala Pro Ala Thr Leu Phe Thr
            260                 265                 270

Asp Ser Asp Asn His Trp Gly Ser Gly Thr Thr Ala Asp Arg Ala Ser
            275                 280                 285

Ala Ala Val Asp Ala Gln Tyr Gly Thr Asp Glu Thr Trp Asp Tyr Tyr
            290                 295                 300

Lys Asn Val His Gly Arg Asn Gly Ile Ala Gly Asp Gly Lys Gly Ser
305                 310                 315                 320
```

```
Tyr Asn Arg Val His Tyr Gly Thr Arg Tyr Asn Asn Ala Phe Trp Asp
                325                 330                 335

Asp Asp Cys Phe Cys Met Thr Tyr Gly Asp Gly Asp Gly Thr Thr Leu
            340                 345                 350

Gly Pro Leu Val Ala Leu Asp Val Ala Gly His Glu Met Thr His Gly
        355                 360                 365

Val Thr Ser Lys Thr Ala Ala Leu Ala Tyr Ser Gly Glu Ser Gly Gly
    370                 375                 380

Leu Asn Glu Ala Thr Ser Asp Ile Phe Gly Thr Leu Val Glu Trp Tyr
385                 390                 395                 400

Ala Asn Asn Ala Ser Asp Pro Gly Asp Tyr Leu Ile Gly Glu Lys Ile
                405                 410                 415

Val Arg Ser Gly Phe Gly Lys Ser Ala Leu Arg Tyr Met Asp Lys Pro
            420                 425                 430

Ser Arg Asp Gly Lys Ser Ala Asp Cys Trp Ser Ser Ser Val Gly Asn
        435                 440                 445

Leu Asp Val His Tyr Ser Ser Gly Val Ala Asn His Phe Ala Tyr Leu
    450                 455                 460

Leu Ala Glu Gly Ser Gly Ala Lys Thr Leu Asn Gly Val Ser Tyr Asn
465                 470                 475                 480

Ser Pro Thr Cys Asp Gly Ser Thr Val Lys Gly Ile Gly Arg Asp Lys
                485                 490                 495

Leu Gly Lys Ile Trp Tyr Arg Ala Leu Thr Val Tyr Met Thr Ser Ser
            500                 505                 510

Thr Asn Tyr Ala Gly Ala Arg Thr Ala Thr Leu Asn Ala Ala Lys Asp
        515                 520                 525

Leu Tyr Gly Ala Gly Ser Thr Glu Tyr Asp Ala Val Ala Ala Ala Trp
    530                 535                 540

Lys Ala Val Asn Val Gly
545                 550

<210> SEQ ID NO 12
<211> LENGTH: 1542
<212> TYPE: DNA
<213> ORGANISM: Micromonospora sp-61168

<400> SEQUENCE: 12
atgcgccgaa ccccctgat gagcggcctc gccacggccg ctctcctggc caccgtcgtc    60
acggtgccca ggcggccac cgccgcaccc accggtaccg ccgacccgtt cacccgcgcg   120
gtcgcccagc tcaaggccca ctccggtgcc ggcctcgccg ccgacggcca gacgttcacc   180
ccccgcaacg tggtgaccga cgccgacggc accgagcacg tccggctcaa ccgctactcc   240
gacggtctgc ccgtcctcgg cggcgacctg gtcgtccacc tcggcaaggg cgactcctgg   300
cgcggcgcca cccaccgcct cgccaacgcc ccgcaacgcg cccgaaggc caagctcagc   360 gaggccgccg ccagcaagat cgcgtacgcc gcatcgaccg ccaccggccg ctccgtggcc   420
ggcgcgcagc tcgtcttcga cgccggtgac accgcgacca ccctcgccta cgaggtggtg   480
gtcggcggca cccacgccga cggcaccccg agcgagctgc acgtgctggt cgacgccacc   540
accgcgcgcg tccgcgactc gtgggagggc gtgcagcggg agggcaccgg caacaccttc   600
cactcgggca cggtctcggt cggcagcaac ctgtccggca gcacctacca gctcgccgac   660
ccggcccggg gcaaccaccg cacctacgac ctcaacggca ggaccagcgg caccggcacc   720
ctggtcacca gcaccaacaa cgtgttcggc aacggcaccc tgaccaaccg gcagaccgcc   780
```

```
gccgccgacg ccgccttcgg cgcgcagaag acctgggact actacaagag cgcgcacggc      840
cgcaacggca tccgcaacga cggcgtcggc gcgtacagcc gggtgcacta cagcagcaac      900
tacgccaacg cgttctggca ggacgcctgc ttctgcatga cctacggcga cggcggttcc      960
ggctggtacc cgctgacctc gctcgacgtg gccgggcacg agatgaccca ggggtcacc     1020 agcaacaccg ccgggctgcg ctacagcggc gagtccggtg gcctcaacga ggccaccagc     1080
gacatcttcg gcaccctggt cgagttctac gcggccagcg ccaaggaccc gggcgactac     1140
ctgatcgggg agaagctgcg cagcaccggc accccgctgc gctacatgga caagccctcc     1200
aaggacggca gtcggcgga ctgctggagc agctcggtcg gcggcctgga cgtgcactac     1260
tcctcgggcg tggccaacca cttcttctac ctgctcgccg tgggcagcgg cacctcctcc     1320
tacggcacca gcacgacctg caacggcacc accatcaccg gcatcggcaa caccaaggcc     1380
ggagcgatct ggtaccgggc gctgacccgc tacatgacca ccaccaccaa ctacaagggc     1440
gcccgcaccg cgaccctgtc ggccgccacc gacctgtacg gcgcgaccag caccgagtac     1500
aagacggtcg ccgccgcctg gcggccgtg agcgtcagct ga                        1542

<210> SEQ ID NO 13
<211> LENGTH: 1659
<212> TYPE: DNA
<213> ORGANISM: Streptomyces thermoalcalitolerans

<400> SEQUENCE: 13
gtgactcccc gctacgcgcg tcccagacgc accgccctgg ccctcgccac cgccgtcgtg       60
gccggagccc tcctcggcac cggtctgagc accggcgcct cggcccagcc ccaggccggt      120
tccaccggcg cggcccccct cgccgccgcc ccgtcctgc tctccgacgc ggagcgcacc      180
tccctgatcc agcaggcgca ggccgacgcc gtcggcaccg cccgggagat aggcctcggc      240
gcccaggaga agctggtcgt cagagatgtc gtcaaggacg ccgacggcac ggtgcacacc      300
cgctacgagc gcacctacgc gggcctgccc gtcctcggcg cgacctgat cgtccacacc      360 tccaggaccg gcaggaccca gggcgtcacc aaggccaccg aggcgaccat caaggtggac      420
acgctcacgc cgaggatcgc cgccgccaag gccgagaagc aggcggtgac cctggcccgg      480
gcggccggct cggagaacac cacccccgac caggccccgc gcaaggtcat ctgggcgggc      540
gacggcacac cggtcctcgc ctacgagacg gtcgtcggcg cctccagga cgacggcacc      600 ccgaacgaac tgcacgtcat caccgacgcg accaccggcg agaagctgta cgagtaccag      660
ggcgtcgtga acggcaccgg cagaaccctg tactcgggca ccgtcaccct ctccaccacc      720
cggtcgggat cgacgtacca gctgtacgac accacgcgcg gcggccaccg gacgtacaac      780
ctggcccgcg gcacctccgg caccggcacc ctgttcaccg acgcggacga cgtgtggggc      840
accggcaccg cctccagttc cagcagcgac cagacggccg ccgccgacgc cgcctacggc      900
gcccaggtca cctgggactt ctacaagaac gtcttcggcc gcaacggcat caggaacaac      960
gggacggccg cctactcacg ggtccactac ggcaacaact acatcaacgc cttctggtcc     1020
gacagctgct tctgcatgac ctacggcgac ggcgcgggca acgtcaagcc gctgacctcg     1080
ctggacgtgg ccgccacga gatgtcccac ggcctcacct cctacaccgc ggggctgcgg     1140
tactccggcg agtccggcgg gctcaacgag gccacctccg acatcttcgg caccggcgtg     1200
gagttctacg ccaacaacgc ctccgacccc ggtgactacc tcatcggcga gaagatcgac     1260
atcaacggca acggcacccc gctgcgctac atggacaggc ccagcaagga cggcgcctcc     1320
gccgactact ggtcctccgg cgtgggcaac agggacgtgc actactcgtc cggcgtcgcg     1380
```

```
aaccacttct tctacctcct cgcggagggc agcggagcga agacgatcaa cggcgtcagc   1440
tacaactcgc cgacgtacga cggctccagg atcaccggca tcggccgcga caaggcgctg   1500
cagatctggt acaaggcgct gaccacgtac atgacgtcga ccaccaccta caagggcgcc   1560
cgcacggcga ccctgaacgc ggcggcgcg ctgtacggct ccggcagcac cgagtacaac   1620
acggtggcgg cggcctggac cgcggtcaac gtcacctga                          1659
```

<210> SEQ ID NO 14
<211> LENGTH: 1659
<212> TYPE: DNA
<213> ORGANISM: Streptomyces ginsengisoli

<400> SEQUENCE: 14

```
gtgactcccc gctacgcgcg tcacaagcgc atcactctgg ccgtcgccac cgctgtcgcc    60
gccggagccc tcctcagcac cggtctgacc accagtgcct cggcccagac cacggccgaa   120
tccaccggcg cggcccacct cgccgccgcc cccaccttcc tgaccaacgc cgcccgcacc   180
tcgctgatcc agcaggcgca ggccgacgcc tccgggaccg cccaggagat aggcctcggc   240
gccaaggagg agttggtcgc cagggacgtc atccaggacg ccgacggcac ggtgcacacc   300
cgctacgagc gcacctacgc cggtctcccc gtcctcggcg gcgacctgat cgtccacagc   360
tccaaggccg gcaagaccca gggcgtgacc agagcgaaca aggcggccat caaggtcgcc   420
acgctcaccc cgaaggtcgc caccgccaag gccgagaagc aggccgtgac cctggcccag   480
gccgccggct cggagaaggt caccgccgac caggccccgc gcaaggtcat ctgggcgggc   540
gacggcacgc cggtcctcgc ctacgagacg gtcgtcggcg gtctccagga ggacggcacc   600
ccgaaccagc tccacgtcat caccgacgcg ccaccggcc agaagctcta cgagtaccag   660
ggcatcgaga ccggcaccgg caagaccctg tactcgggca ccgtcagcct gaccaccacc   720
ctgtcggggt cgacgtacca gctctacgac accacccgcg gcggtcacaa gaccaacaac   780
ctggcgggga agacctcggg caccggcacc ctgttcacca acaccaccga cgtgtggggc   840
accggcaccg cctccagctc caccaccgac cagacggccg ccgcggacgc cgcctacggc   900
gcccagacga cgtgggactt ctacaagaac accttcggcc gcaacggcat caagaacaac   960
ggcgtgggcg cctactcccg ggtccactac ggcaacaact acgtcaacgc cttctgggac  1020
gacagctgct tctgcatgac ctacggcgac ggctcgggca cacccacccc gctgacctcg  1080
ctggacgtcg ccggccacga gatgagccac ggcgtcaccg ccgccaccgc caagctgaac  1140
tactccggcg agtccggcgg tctgaacgag gccacctccg acatcttcgg caccggcgtg  1200
gagttctacg ccaacaacgc ctcggacccc ggtgactacc tcatcggtga agatcaac    1260 atcaacggca acggcacccc gctgcgctac atggacaagc ccagcaagga cggcggctcc  1320
gccgactact ggtcctccac cgtgggcagc aaggacgtgc actactcgtc cggcgtcggg  1380
aaccacttct tctacctcct cgcggagggc agcggcgcga agacgatcaa cggcgtcagc  1440
tacaactcgc cgacgtacaa cggcgccacg gtcaccggca tcggccgcgc caaggcgctg  1500
cagatctggt acaaggcgct caccacgtac atgacgtcga ccaccaacta caaggccgcc  1560
cgcacggcga ccctgaacgc ggcgtcgcg ctgtacggct ccggcagcac cgagtacaac  1620
acggtcgcgg cggcctggac cgcggtcaac gtgacctga                         1659
```

<210> SEQ ID NO 15
<211> LENGTH: 2043
<212> TYPE: DNA

<213> ORGANISM: Kribbella aluminosa

<400> SEQUENCE: 15

```
gtggccgtcg tcgcggcagc gggtcttgcg acgactttca ccgcctcgac cgcgggcgcc      60
gccgaccgga cggctccgct cccaggcttc aaccagccgg ccgccgtcca ggccgagcag     120
gcgctgaccg cgcggacggc cgcggctctc ggtctcggca ccggcgagca gctcaaggtc     180
cgcgacgtgg tgaaggaccc ggacggcacg gagtacgtcc gctacgaccg caccttcaac     240
ggcctcaagg tcgtcggagg tgacctgatc gtcaagcgca agggcgagtc gatcggccag     300
gtcacgtaca accgcggcgc caaggccgtc gccgtcgcca ccaagccgac gctgtcccag     360
tcggcggcgc tcgcgaaggg tgcgcaagcc gcggagttca aggccaccgg caacaagggc     420
gagttggtcg tcttcgtgac gccgaccaag cctgtcctgg cgtacgaggt cgtgaccacc     480
ggtgtgaagg ctgaccagac cccttcggtg ctgcactcgt tcatcgacgc caagaccggc     540
gccgtgctcg accaggacga cgaggtcaag accggtaccg gcaactcgat gtactccgga     600
accgtcagca tcggtacgtc ggggagctac acgatgagcg acccgacccg cggcggcaac     660
tacaccacgg acctcaacgg ctccacctcc ggcagcggta cgacgttcac cgaccctgac     720
gacacctggg gcaacggctc gacgtccagc cgccagaccg ccggtgtgga cgcgcattac     780
ggcgcccagc tgacctggga ctactacaag aacgtccacg gccggaacgg catcttcaac     840
aacgccagg gcgcgcggtc ccgcgtgcac tacggcaacg cgtacgtcaa cgcgttctgg     900
gacggcaccc agatgacgta cggcgacggc gcgagcaacg cccgtccgct gacctcgatc     960
gacgtcgccg ccacgagat gagccacggc gtcaccgagg cgaccgcgaa cctcaactac    1020
tccggtgatg cgggcggcct gaacgaggcg acctcggaca tcttcggtac ggcggtggag    1080
ttctccgcga caactcgtc cgacccgggt gactacctga tcggcgagaa gatcaacatc    1140
aacggcaacg gcacgccgct gcgctacatg gacaagccgt cgaaggacgg ccgcagcgtg    1200
gactgctggt cgaccagcac cggcggcctg gacccgcact actcgtccgg cccgctgaac    1260
cactggttct acctggcctc cgagggcacc ggcagcaagg tcatcggcgg cgtcacgcac    1320
agcagcaccg cctgcaacgg cgcgaccatc accggtgtcg gccgcgacgt ggccgccaag    1380
gtctggtacc gcacgctcag caccaagctg agctcgggca gcacctacaa ggacgcccgc    1440
gagggtgcga tcaactccgc gaaggagctg tacggcgcgg actcggcgca gtgcaagggc    1500
atcgaggccg cgttcaacgg catctcggtc ccggctggtg cggccgcctg tggtggcggg    1560
accgacccgg agccgccgac gggtggcaac ctgctgaaga cccgggttt cgagtccggc    1620
gcggtggact ggaccggcac cgccggcccg atcaccaacg actcgggccg cccggcccgg    1680
accggcactt ggaagctctg gctcggaggg aacggccgca ccgtcaccga gaacgtcgga    1740
cagtcggtcg cgatcccggc gtcggcgacc agcgcgaccc tgtcgttctg gatccggatc    1800
gacaccgcgg agaccacctc ttcgacggtg tacgaccggg cgttggtgca gatcgtcgac    1860
gggtcgacca cgaccacgct ggcgacgtac tcgaacctga caagaacac gtcgtacatc    1920
cagaagacgc tgaacgtgac ggcgtacaag ggaaagaccg tgacggtgaa gttcgtcggc    1980
caggaggact cctcgctgca gaccagcttc gtcatcgacg cacctccct gaccgcgagc    2040
tga                                                                 2043
```

<210> SEQ ID NO 16
<211> LENGTH: 2040
<212> TYPE: DNA
<213> ORGANISM: Streptomyces sp-61982

<400> SEQUENCE: 16

```
ttgagaagca gatcctctcg cagacgcacc ccccacaccc ccgcccaccg cgccgccgcc      60
gtcgccctcg tcggtgtctc cgcgctcctc gccgccgccg tccagtcggg cgccgcgagc     120
gccacgccca ccgaggcgac cgtggggaag acgaacctgg cccatgtcgc cgcgaagctc     180
accccctcgc agcgggccga actgatccgc gacgcggacg gcgccaaagc gcgcacggcg     240
aaggacctcg gcctcggcgc ccaggagaag ctggtcgtca aggatgtgat caaggacgcc     300
gacggcaccc tccacacccg ctacgagcgc acctacgccg gcctgcccgt cctgggcggc     360
gacctgatcg tggacaccgc caagtccggg cagacggagc gggtcctgaa agcgacgaac     420
gcgaccgtga aggtcgcgag cctcactccg cgcgtgtcga aggcgaccgc ggagcagcag     480
gccgtccagc gcgccaaggc gctgggcagc accaaggcgg tcgagcagtc gtcccgcaag     540
gttgtctggg cggcaagcgg caagcccgtc ctcgcctacg agacggtgat cggcggcttc     600
caggacgacg gcaccccaa cgcgctgcac gtcatcaccg acgcgagcac cggcaaggag     660
ctcttccgcc accagggcat cgagaccggc atcggcaaca cccagtacag cggccaggtg     720
acactgacga cgacccagtc gggttcgacg tacacgctga cgacggcgc gcgcggcggc     780
cacaagacgt acaacctcaa ccacggctcc tccggcaccg ggacgctgtt ctcgcagtcc     840
agcgacacct ggggcaacgg cacgacgtcg aacgccgcca ccgcgggcgc cgacgcgcac     900
tacggcgcac aggagacctg ggacttctac aagaacacct tcggccgcaa cggcatcaag     960
aacgacggca cggcggccta ctcgcgggtc cactacggca actcgtacgt gaacgcgttc    1020
tgggacgaca gctgcttctg catgacctac ggcgatggtt cgggcaacgc cgacccgctg    1080
acctctctcg acgtggcggg ccacgagatg agccacggtg tcacctccaa caccgcgggc    1140
ctcgactaca gcggcgagtc cggcggcctg aacgaggcca cctccgacat catgggcacc    1200
ggcgtggagt tctacgccaa caacagcacg gacgtcggtg actacctcat cggcgagaag    1260
atcaacatca acgcgacgg caccccgctg cgctacatgg acaagccgag caaggacggc    1320
ggctccgccg actcctggtc tcaggtgtc ggcaacctcg acgtgcacta ctcgtccggt    1380
gtcgccaacc acttcttcta cctcctcagc gagggcagcg cgccaaggt gatcaacggc    1440
gtcagctaca actcgccgac ggccgacggc ctgccggtca ccggcatcgg gcgcgacaag    1500
gcgctgcaga tctggtaccg ggcgctcacc acgaagttca cctcgaccac caactacgcc    1560
ggcgcccgca cgggcacgct cgcggcggcg ggcgagctgt acggcacctc cagcgccgag    1620
tacaaggcgt gcaggacgc gtgggcggcg gtcgcggtcg ggtcgcgctc cggcggtggc    1680
agcggcggcg gtacgtcgta cgagaacacg tccccggtgt ccattccgga caacggtccc    1740
gcggtgacgt cgtcgatcac cgtgtccggc aggaccggga acgcgccaag cagcctccag    1800
gtcggcgtcg acatcacgca cacctggcgc ggcgacctcg tgatcgacct ggtgggcccc    1860
tccggcacct cctaccgcct gaagaacttc agctcgtcgg actcggcgga cgacgtcaaa    1920
gagacctaca cggtcaacgc ttcctccgag acggccaacg ggacctggaa gctgaaggtc    1980
caggaccagg ccgcgcagga cgtcggcacc ctcaacagct ggaagctgac cttcccgtag    2040
```

<210> SEQ ID NO 17
<211> LENGTH: 1530
<212> TYPE: DNA
<213> ORGANISM: Kribbella aluminosa

<400> SEQUENCE: 17

| | |
|---|---|
| atgaagcgca tccatcgcgc cggtctcgcc gcgacggcga tcgccggcct ggccgtcgcc | 60 |
| tccatcaccg ccaccgtgca ggccgcccag cccggcagtg gccagcggt gtcgccggtc | 120 |
| gccgctgctc gcgccaacgc cgcacagctc ggcctcggcg acgccggtga catggtcgtc | 180 |
| cgcgacgtcg tcaccgacgg cgacggcagc acccacgtcc ggttcgaccg cacctaccag | 240 |
| ggcctgccgg tcgtcggcgg cgatgtcgtc gtacaccagg acaaggccgg caaggcccgt | 300 |
| tcgtccagcg gcggcgtcgg caagctgagc ctgtcgacca gccgactgc gtccgccgcc | 360 |
| accgcgttcg ccgccgccaa gacgaaaagc agcaagcagc agctcgtcgt cttcgtcaca | 420 |
| aacgccggcc aggccaagct cgcctacaag gtcgtcagcg aaggccgcaa ggccaacggc | 480 |
| gagccgaccg gcaccgagac ctacgtcgac gcgcagaccg gcaaggtcct cgacagctgg | 540 |
| accaccgtcc acgaagacct cggcagcggc accggcctgt acgtcggcac cgtcggcctg | 600 |
| gacaccacca gtccggcac aggctggacc atggtcgacc cggtccgcgg cggcaacgcg | 660 |
| acgtacaacg ccggcacgct gttcagcgac gccgacaacg tgtgggggag cggcagcaac | 720 |
| tcgaacccgc agtcggccgg tgtcgacgcg cactacggca tcgccgagac gtgggactac | 780 |
| tacaagaacg tgcacagccc caacggcatc gccaacgacg gcaagggcgc gaagtcgtac | 840 |
| gtccacgacg gcgcgtacgt gaacgcctcc tggagtgact cgtgcttctg catgcggtac | 900 |
| ggcgacggcg acccgagcca gggcatcggc ccgctggtcg agctggacat cgccgggcac | 960 |
| gagatgagcc acgcgtcac cagccgctcg gccggcctgc gctacagcgg cgagtccggt | 1020 |
| ggtctcaacg aatccacctc ggacatcttc ggcacggccg tcgagtggta cgccaacaac | 1080 |
| agccaggacg cccccgacta cgtgatgggt gaggagatct tcaccgacta caacccggcg | 1140 |
| gtgaactaca tccggcggat ggacaagccg tcgatggacg gcgccagcgc cgactcgtgg | 1200 |
| tcgcgcagcg tcggccggct gaacgtgcac tactcgtccg gcgtcggcaa ccacttcttc | 1260 |
| tacctgctgt cggagggcag cggtgcgaag acgatcaacg gcgtcgcgta caacagcccg | 1320 |
| accgcgaacg gcgtcacggt caccgggatc ggcatcacca aggccgagaa gatctggtac | 1380 |
| cgcgcattga cgacgtacat gacgtcgcgg acggactacc acggcgcccg tacggcgacg | 1440 |
| ttgaacgcgg cgacggatct ctacggtgcg agcagcccgg agcgggccgc ggtcgacaag | 1500 |
| gcttgggccg cagtgaacgt tctgccgtaa | 1530 |

<210> SEQ ID NO 18
<211> LENGTH: 2022
<212> TYPE: DNA
<213> ORGANISM: Streptomyces champavatii

<400> SEQUENCE: 18

| | |
|---|---|
| ttgagaccca cctcccaccg gcgcgccgtc gccggcggcg ccctcgccgc cgtcaccgcg | 60 |
| ctgctcgccg tcaccgccac cacggccccg gcgaccgcgg ccgatccgc accggccgcc | 120 |
| aagcccaccg cggcgcgtac cggcgccctc ccggccgacc tcagcccgc ccagcgcgcc | 180 |
| gccctgatcc gcgccgccga ggcgaagacc gcctccgtcg ccgccgaact cggcctcggc | 240 |
| gcacaggaga agctgctcgt ccgcgacgtg gtcaaggacc gcgacggcac cctgcacacc | 300 |
| cgctacgagc gcacctggtc cggactcccc gtgctcggcg gtgacctggt cgtcgccgcc | 360 |
| gagcccgacg gcacgcccgc gacggtgacc aaggcgtccc gcaacgccct caagggcatc | 420 |
| gccaccaagg cggagatcgc cccctcggcc gcgaagaagc aggcgctgaa cgccgccgag | 480 |
| gcccacgacg cggagaaggc cgccaccgac ggcgccccc gtcaggtggt ctggaacgcc | 540 |
| gacggcaagc cggtcctcgc cttcgagacg gtggtcggcg gactccagca cgacggcacc | 600 |

```
cccaacgaac tgcacgtcgt caccgacgcc gccaccggcg agaagctcca cgagtggcag        660
gccgtcgaga acggcaccgg caacacccag tacagcggca ccgtcaccct cggcagcacc        720
aagtccggct ccacctggaa cctgaccgac gccgggcgcg gcaaccaccg caccaacaac        780
ctcaaccgct ccacctcggg caccggcacc ctcttctccg gccccgacga cgtctggggc        840
aacggcctgg cgagcaacac cgagaccgcc gccgccgacg ccgcctacgg cgcccaggcc        900
acctgggact actacaagga cgtccacggc cgctccggca tccggggcga cggcgtcggc        960
gcgtactcgc gcgtccacta cggcaacaac tacgtcaacg ccttctggac cgactcctgc       1020
ttctgcatga cctacggcga cggcgcgggc aacgccgccc cgctcacctc gctcgacgtc       1080
gccgcccacg agatgaccca cggcctgacc tccgtcaccg ccaagctcgt ctactccggc       1140
gagtccggcg cctcaacga ggcgaccagc gacatcctcg ccgccgccgt cgagttccac        1200
gagaacaacg ccgccgacaa gggcgactac ctcatcggcg agaagatcga catcaacggc       1260
aacggcaccc cgctgcggta catggacaag ccctcccgcg acggcaagtc caaggactcc       1320
tggtactccg gcatcggctc cgtcgacgtc cactactcct cgggcccggc caaccacttc       1380
ttctacctgc tctccgaggg cagcggggcc aagacggtca acggcgtcag ctacgactcg       1440
ccgaccgccg acggcctgcc cgtcaccggc atcggccgcg acaaggccgc gctgatctgg       1500
ttcaaggccc tcaccaccaa gttcacctcc acgaccaact acgccggggc cgcaccggc        1560 accctggccg tcgccggtga gctgtacggc accagcagcg ccgagtacaa ggccgtccag       1620
gacgcctggg ccggcgtcgc ggtcggcgcc gctccggcg gcggcagcgg cggcaccacc        1680
ttcgagaaca ccacggccgt cgccatcccc gacgccggcg ccgcggtcac ctcggacatc       1740
accgtcaccg gccgcaccgg caacgccccc gccgccctcc aggtcaccgt cgacatcagc       1800
cacacctggc gcggcgacct cgtcatcgac ctggtcggcc caacggcac cgcctaccgg        1860 ctgaagaacg ccagctcctc ggactcggcc gacaacgtcc aggagaccta caccgtcaac       1920
gcctccgcgc agaccgccaa cggcacctgg aagctccgcg tccaggacac cgcccgctcg       1980
gacaccggcc gcatcaacag ctggaagatc gtcctgccgt aa                          2022
```

<210> SEQ ID NO 19
<211> LENGTH: 1650
<212> TYPE: DNA
<213> ORGANISM: Streptomyces kathirae

<400> SEQUENCE: 19

```
atgagtcgga tacggcacat ccgagaatcc cgtctcgccg cggccggaac cgccgcgacc         60
accgcggccc tgctggccgc ggctctcgcc ccggcccccg cgccgccgc ggccgacaga         120 cccgccgggg ccaccgcgat cagcaacgcc gcggccgcgc tggtgcacca ggccacgcgc        180
ctgggcctga cgtccgcgca gggtaccagc gtccgtgacg tcgtcgtgga tccggacggc        240
agccagcatg tgcgctacga ccggacgttc cgtgacatcc ccgtcctcgg cggcgacttc        300
gtggtccacc tggcgccggg cgggtccttc cgcagcgccg accgggccac cgagcgcgcc        360
atctccgtgc cgacgaccac ccccacggtc aaggctcccc gggccgccga cctggcagcc       420
tccgccctgc gcgccgcgaa cgccggcgag ctgctgaaga acgtgaccgc caagccgcag       480
ctcgtcgtcg acgcgctgca cggcgcgccc cggctcgcct ggcgcaccaa tgcggcgggc       540
caggactcgc tcggcaaccc ggtcgcccgc acggtcctca cggacgcccg caccggcaag       600
cagatcgacg cgtgggacag catcgagacg gcgaccggcg acggcaagtc cctctacagc       660
```

```
ggcacggttc cgctgcagac gacgcagtcc gggtcgacgt accagctcaa ggacccgacg      720
cgcggcaaca cctacacggg cgacgccgcg aacaagacgg acctgtgcgt cctcagcatc      780
tgcttcagcc gcgcaccggc caccctgttc accgactccg acaaccactg gggcacgggc      840
accacctcgg accgctcgtc cgcggcggtg gatgcgcagt acggcacgaa cgagacctgg      900
gactactaca agaacgtcca cggccgcaac ggcatcgcgg gcgacggcaa gggctcgtac      960
aaccgtgtgc actacggcac cgactacaac aacgccttct gggacgacaa ctgcttctgc     1020
atgacgtacg gcgacggcga cgggacgacg ttcggcccgc tggtggcgct ggacgtggcg     1080
gggcacgaga tgtcgcacgg cgtgacgtcg aagaccgcgg ccctgacgta ctccggagag     1140 tcgggggtc tgaacgaggc gacctcggat gtcttcggga cgctggtgga gtggtacgcg     1200
aacagcccct ccgaccccgg tgactacctc atcggcgaga agatcgtccg ctcgggcttc     1260
ggcaagtcgg cgctgcggta catggacaag ccgtccaagg acgggaactc ggcggactgc     1320
tggagttcgt cggtcgggaa tctcgacgtc cactactcct cgggcgtcgc gaatcacttc     1380
gcgtacctgc tcgccgaggg cagcggtgcg aagaccgtca acggggtcgc ctacgactcc     1440
cccacctgca acggctccac ggtcaccggg atcggccggg acaagctggg gaagatctgg     1500 taccgcgcg tgacggtcta catgacgtcc tcgacgaact acgcgggcgc ccggacggcg     1560
accctgagcg cggcgaagga cctctacggc gccggcagca ccgagtacaa cgcggtggcg     1620
gcggcatgga gcgccgtgaa cgtgaactga                                     1650

<210> SEQ ID NO 20
<211> LENGTH: 2004
<212> TYPE: DNA
<213> ORGANISM: Streptomyces kathirae

<400> SEQUENCE: 20
gtgagacgta taccccgtca ggcgacggcg gccggcgccc tggtggcgac cgccgccttc       60
ctcgccgtcg gcatgcaggc ggctcccgcg accgccaagc ccgctccccca cgccgactcc      120 ctgcgcacag gggggctgga agccgagctc accggagccc agcacaccgc gctgctccag      180
agcgcggccc ggaccacgac gcagaccgca cggtccatcg gcctgggctc gaaggagaag      240
ctggtcgtca aggacgtcgt caaggacaac gacggtacgc tccacacccg ttacgagcgc      300
acctacgacg gtctgccggt gctcggcggc gacctgatcg tgcacacccc gccggcctcc      360
ctggccgccg gcgccgtgag caccaccttc aacaacaagc acgccatcaa ggtcgccacg      420
accacggcgc cgttcaccaa gtcggccgcc gagacgaagg cgctcaaggc ggcgaaggcc      480
ctggacgcca agaagcccgc cacggacagc gcccggaagg tgatctgggc cggcaacggc      540 accccccaagc tcgcctggga cacggtgatc ggcggtttcc aggacgacgg cacacccagc      600
caactgcatg tcgtcaccga tgccacgacc ggcaaggagc tctaccgcta ccagggcatc      660
aagaccggta ccggcaacac ccagtacagc ggcacggtga cactcaacac gacgctgtcc      720
ggctcgacct accagctcaa cgacaccacg cgcggcggcc acaagacgta caacctcaac      780
aacggcacct cgggcaccgg caccctgatg accgactcgg acgacgtctg ggcaacgga      840 tccgggtcca acagccagac ggccggtgcg gacgccgcct atggcgcgca gatgacatgg      900
gacttctaca agaacacctt cgggcgcagc ggcatcagga acgacggcgt cgcggcctac      960
tcccgcgtcc actacagctc ggcctacgtc aacgccttct gggacgacag ctgcttctgc     1020
atgacgtacg gcgacggctc gggcggtacc cacgcgctga catcgctgga cgtggcgggt     1080
catgagatga gccacggtgt cacctccaac accgccggcc tcaactacac cggggagtca     1140
```

```
ggcggcctca acgaggcgac ctccgatgtc ttcggcacgg gtgtcgagtt ctacgccaac     1200
aacagctccg acccgggcga ctacctcatc ggcgagaaga tcgacatcaa cggtgacggc     1260
accccgctgc gctacatgga caagcccagc aaggacggcg cctcggccga cagttggtac     1320
tccggtgtcg gcaacctgga cgtgcactac tcctcggggc cggcgaacca tatgttctac     1380
ctgctctccg agggcagcgg aaccaaggtc atcaacggcg tgacctacaa cagccccacc     1440
tcggacggcg tggccgtcac gggcatcggc agagccgccg cgctgcagat ctggtacaag     1500
gcgctgacga cgtacatgac gtccagcacg aactacgccg ccgcccgcac cgccgccctc     1560
aacgccgcag cggccctgta cggcaccaac tccacccagt acgccggagt gggcaacgcc     1620
ttcgccggga tcaacgtcgg aggccacatc acgccgccct cctcgggagt gacggtcacc     1680
aacccgggca gccagtcctc gaccgtgggt accccggtga gcctgcagat tcggcgtcc      1740 agcaccaaca gcggcgcgct cacctacagt gcgaccggac tgccggccgg cctgtcgatc     1800
aacagctcga cgggcgtcgt ctccggcact ccgaccacgg cgggcaccta cagcaccacg     1860
gtgaccgtga ccgacagcac gggtgccacc ggcaccgcga gcttcacctg gacggtcagt     1920
tcctccggcg gaggcacatg cacctccagg caactgctgg gcaacccggg cttcgagtcg     1980
ggcaacacca cctggaccgc ctaa                                            2004

<210> SEQ ID NO 21
<211> LENGTH: 1650
<212> TYPE: DNA
<213> ORGANISM: Streptomyces sp-62237

<400> SEQUENCE: 21
gtgagccccc tctacgcgcg tcacaagcgc accactctgg ccgtagccac cgctgtcgcc       60
gccggcgccc tgctcaccac gggcctgacc accaacgcca ccgccgccgc gaagcagcca      120
ctggccgccg cccccaccct gctctccaac tccgcccgca ccgcgctgat ccagaaggcg      180
caggcggacg tcgcggagac cgcgcaggag ataggcctgg gcgccaagga gaagctggtc      240
gtcaaggacg tcgtgaagga cgtcgacggc accgtccaca cgcgctacga gcgcacctac      300
gcgggcctgc ccgtgctcgg cggcgacctg gtcgtgcaca cctccaagtc cggcaagtcc      360
gagggcgtca cccgggcgac caaggcgacc atcaaggtgg cctcgctcaa gccggggatc      420
agcaccgcca aggcggagaa gaccgcgctc accgccgcca aggcgctggg ctccgccaag      480
tccgcggccg acggcgcccg caaggtcatc tgggccggct ccggcacccc cgtcctcgcc      540
tacgagacgg tcgtcggcgg cttccaggac gacggcaccc cgaaccagct gcacgtcatc      600
accgacgcgg cgaccggcaa gaagctcttc gagtaccagg gcatcgagaa cgccaccggc      660
accggcaaga ccctgtactc gggcacggtc agcctcacca cgaacctgtc gggctcgacg      720
taccagctgt acgacaccac gcgcggcggc cacaagacgt acaacctgag ccacggcacc      780
agctcgggca ccggcacccct gttcacggac gcggacaacg tctggggcac cggcgccgcc      840
tccagctcca gcaccgacca accgcggcc gccgacgccg cctacggcgc gcaggagacc      900
tgggacttct acaaggacac cttcggccga agcggcatca agaacaacgg cgtgggcgcc      960
tactcccggg tccactacgg cagctcctac gtcaacgcct tctgggacga cagctgcttc     1020
tgcatgacct acggcgacgg ttccagcaac acccacccgc tgacctcgct ggacgtggcc     1080
ggccacgaga tgagccacgg tgtcaccgcc aacaccgccg gcctcaacta cagcggtgag     1140
tccggcggcc tgaacgaggc cacctcggac atcttcggca ccggtgtgga gttctacgcc     1200
```

```
aacaactcct ccgacgtcgg cgactacctc atcggcgaga agatcaacat caacggcgac    1260
ggcaccccgc tgcgctacct ggacaagccc agcaaggacg gcgcctccgc cgactactgg    1320
tcctcgtcgg tgaagaacct ggacgtgcac tactcgtccg gtgtcgcgaa ccacttcttc    1380
tacctgctgt ccgagggcag cggctcgaag acgatcaacg gggtgtccta caactccccg    1440
acgtacaaca gctccacggt caccggcatc ggccgcgcca aggcgctgca gatctggtac    1500
aaggcgctga cgacgtactt cacgtcgacc accaactaca agtcggcgcg caccgggacg    1560
ctctcggcgg cggccgccct gtacggctcg ggcagcaccg agtacaacgc ggtggcggcg    1620
gcctggacgg ccgtcaacgt cacctcgtga                                    1650
```

<210> SEQ ID NO 22
<211> LENGTH: 1653
<212> TYPE: DNA
<213> ORGANISM: Streptomyces sp-61982

<400> SEQUENCE: 22

```
atgagtcgga tacggcacgc ccgaggttcc cgtctaaccg ccgccggcac cgccgcgacc      60
gccgcggctc tgctgggcgc cgccctcgct cccgcgccca ccgccggcgc ggccgaggga    120
ccgagcaggg ccaccgcgat cagcaacgcg acggcggtgc tggaccgcct gggcgcccaa    180
ctgggcctga cggcggctca gggcaccagc gtgcgggacg tcgtcgtgga cccggacggc    240
agccagcacg tgcgctacga ccggacctac cgtcagctgc ccgtgctcgg cggcgacttc    300
gtggtccacc tggcgccgga cggctcctac cgcagcacgg accgcgccac caagcggtcc    360
gtctccctgt cgacgatcac gcccacggtc agggctccca gggccgccga cctggccgcg    420
accgcgctgc gcgccgcgaa cgccggggag ctgctgaaga cgtgaccgc aaagccgcag    480 ctcgtcgtgg acgcaactca cggcgcgccc ggctggcct ggcgcaccga cgcggtgggc    540
aaggactcgc tcggcaaccc ggtcgcccgc acggtcgtca cggacgccct caccggccgg    600
cagatcgacg cctgggacag catcgagacg gcgaccggcg acggcaagtc cctctacagc    660
ggcacggttc cgctgcagac cacgcagtcc gggtcgacgt accagctcaa ggaccccacg    720
cgcggcaaca cgtacacggg cgacgccgcg aaccagaccg acctgtgctt cctcaccctcc    780 gtctgcgtca gccgcgcccc cgccaccctc ttcaccgact cggacaacca ctgggggttcg    840 ggcaccacgg cggaccgcgc gtcggcggcc gtggacgcgc agtacggcac cgacgagacg    900
tgggactact acaagaacgt ccacggccgc aacggcatcg cgggcgacgg caagggctcg    960
tacaaccgcg tccactacgg caccaggtac aacaacgcct ctgggacga cgactgcttc    1020 tgcatgacgt acggcgacgg cgacgggacg acgctcgggc cgctggtggc gctggacgtg    1080
gccggccacg agatgacgca cggcgtgacg tccaagacgg cggcgctggc gtactccggc    1140
gagtcgggcg gcctcaacga ggccacctcg gacatcttcg gcaccctggt ggagtggtac    1200
gcgaacaacg cctccgaccc cggtgactac ctgatcggcg agaagatcgt ccgctccggc    1260
ttcggcaagt cggcgctgcg ctacatggac aagccgtcca gggacggcaa gtcggcggac    1320
tgctggagca gttcggtggg caatctggac gtccactact cctccggcgt ggcgaaccac    1380
ttcgcatacc tgctcgcgga gggcagcggc gcgaagaccc tcaacggtgt cagctacaac    1440
tcgcccacct gcgacggctc cacggtgaag ggcatcggcc gggacaagct cggcaagatc    1500
tggtaccggg cgctgacggt ctacatgacg tcctcgacga actacgcggg cgcgcgcacg    1560
gcgacattga acgcggcgaa ggacctctac ggggccggga gcacggagta cgacgcggtg    1620
gcggctgcct ggaaggccgt gaacgtgggc tga                                1653
```

```
<210> SEQ ID NO 23
<211> LENGTH: 27
<212> TYPE: PRT
<213> ORGANISM: Bacillus clausii

<400> SEQUENCE: 23

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala
            20                  25
```